United States Patent

Fritz et al.

[11] Patent Number: 5,942,536
[45] Date of Patent: Aug. 24, 1999

[54] N-[2-SUBSTITUTED-3-(2-AMINOETHYL)-1H-INDOL-5-YL]-AMIDES: NEW 5-HT$_{1F}$ AGONISTS

[75] Inventors: James E Fritz, McCordsville; Patric J Hahn, Indianapolis; Stephen W Kaldor, Indianapolis; Miles G Siegel, Indianapolis; Yao-Chang Xu, Fishers, all of Ind.

[73] Assignee: Eli Lilly and Company, Indianapolis, Ind.

[21] Appl. No.: 09/043,360

[22] PCT Filed: Oct. 8, 1996

[86] PCT No.: PCT/US96/16122

§ 371 Date: Mar. 13, 1998

§ 102(e) Date: Mar. 13, 1998

[87] PCT Pub. No.: WO97/13512

PCT Pub. Date: Apr. 17, 1997

Related U.S. Application Data

[60] Provisional application No. 60/005,213, Oct. 10, 1995, and provisional application No. 60/015,851, May 22, 1996.

[51] Int. Cl.$^6$ .................. A61K 31/405; C07D 209/08
[52] U.S. Cl. .................. 514/414; 514/415; 548/467; 548/491
[58] Field of Search .................. 514/414, 415; 548/467, 491

[56] References Cited

U.S. PATENT DOCUMENTS

| | | | |
|---|---|---|---|
| 3,472,870 | 10/1969 | Larsen et al. | 260/326.12 |
| 3,591,603 | 7/1971 | Papanastassiou et al. | 260/326.15 |
| 3,915,990 | 10/1975 | Smythies | 260/326.15 |
| 4,544,663 | 10/1985 | Manning et al. | 514/378 |
| 4,636,521 | 1/1987 | Coates et al. | 514/415 |
| 4,672,067 | 6/1987 | Coates et al. | 514/323 |
| 4,803,218 | 2/1989 | Stanley et al. | 514/414 |
| 4,839,377 | 6/1989 | Bays et al. | 514/415 |
| 5,030,640 | 7/1991 | Fisher et al. | 514/339 |
| 5,276,051 | 1/1994 | Lesieur et al. | 514/315 |
| 5,298,520 | 3/1994 | Baker et al. | 514/383 |

FOREIGN PATENT DOCUMENTS

| | | |
|---|---|---|
| 438230 | 7/1991 | European Pat. Off. |
| 490263 | 6/1992 | European Pat. Off. |
| 634398 | 1/1995 | European Pat. Off. |
| 91/18897 | 12/1991 | WIPO |
| 92/13856 | 8/1992 | WIPO |
| 93/11106 | 6/1993 | WIPO |
| 94/03446 | 2/1994 | WIPO |
| 94/10171 | 5/1994 | WIPO |
| 94/14770 | 7/1994 | WIPO |

OTHER PUBLICATIONS

Macor, John, Presentation: "Serotonin in Neuroscience", Philadelphia, Sep. 27–29, 1994.

Taylor, et al., *Molecular Pharmacology*, 34, 42–52, 1988.

*Primary Examiner*—Joseph K. McKane
*Attorney, Agent, or Firm*—Robert D. Titus

[57] ABSTRACT

The invention provides novel 5-HT$_{1f}$ agonists of formula (I) where X, $R^1$, $R^2$, and $R^3$ are defined in the specification, which are useful for the treatment of migraine and associate disorders.

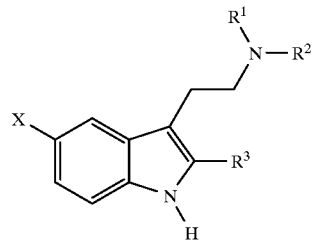

(I)

13 Claims, No Drawings

N-[2-SUBSTITUTED-3-(2-AMINOETHYL)-1H-INDOL-5-YL]-AMIDES: NEW 5-HT$_{1F}$ AGONISTS

This application is a 371 of PCT/US96/16122 filed Oct. 8, 1996, and based on provisional application No. 60/005,213 filed Oct. 10, 1995 and provisional application No. 60/015,851 filed May 22, 1996.

Theories regarding the pathophysiology of migraine have been dominated since 1938 by the work of Graham and Wolff (*Arch. Neurol. Psychiatry,* 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.,* 600, 587–600 (1990)). Recent work by Moskowitz has shown, however, that the occurrence of migraine headaches is independent of changes in vessel diameter (*Cephalalgia,* 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology,* 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA,* 90, 408–412 (1993)). This 5-HT$_{1F}$ receptor exhibits a pharmacological profile distinct from any serotonergic receptor yet described. The high affinity of sumatriptan at this subtype, $K_i=23$ nM, suggests a role of the 5-HT$_{1F}$ receptor in migraine.

This invention provides novel 5-HT$_{1F}$ agonists which inhibit peptide extravasation due to stimulation of the trigeminal ganglia. Although structurally similar compounds have been shown to be potent vasoconstrictors (U.S. Pat. No. 4,839,377), the compounds of the present invention exhibit no appreciable vasoconstrictive properties. The lack of vasoconstrictive properties, coupled with potent 5-HT$_{1F}$ agonist activity, distinguish the compounds of the present invention over structurally similar compounds and currently available migraine therapies.

The present invention provides a method for increasing activation of the 5-HT$_{1F}$ receptor by administering to a mammal in need of such activation a pharmaceutically effective amount of a compound of Formula I:

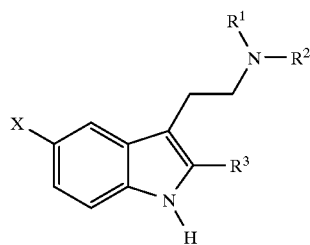

I in which

R$^1$ is hydrogen or C$_1$–C$_4$ alkyl;

R$^2$ is C$_1$–C$_4$ alkyl, C$_3$–C$_8$ cycloalkyl, cycloalkyl-(C$_1$–C$_3$ alkylene), aryl-(C$_1$–C$_3$ alkylene), or heteroaryl-(C$_1$–C$_3$ alkylene);

R$^3$ is hydrogen or C$_1$–C$_4$ alkyl;

X is R$^4$C(O)NH—, R$^5$R$^6$NC(Y)NH—, R$^7$OC(O)NH—, or R$^8$SO$_2$NH—;

R$^4$ is C$_1$–C$_4$ alkyl, C$_3$–C$_7$ cycloalkyl, phenyl, substituted phenyl, biphenylyl, naphthyl, or a heterocycle;

R$^5$ and R$^6$ are independently selected from the group consisting of hydrogen, C$_1$–C$_6$ alkyl, C$_3$–C$_6$ alkenyl, C$_3$–C$_8$ cycloalkyl, phenyl, substituted phenyl, phenyl (C$_1$–C4 alkylene), phenyl(C$_1$–C$_4$ alkylene) substituted in the phenyl ring, ((C$_1$–C$_4$ alkyl or C$_1$–C$_4$ alkoxycarbonyl substituted) C$_1$–C$_4$ alkyl)phenyl, C$_1$–C$_4$ alkyl α-substituted with C$_1$–C$_4$ alkoxycarbonyl; or R$^5$ and R$^6$ taken together with the nitrogen atom to which they are attached form a pyrrolidine, piperidine, piperazine, 4-substituted piperazine, morpholine or thiomorpholine ring;

R$^7$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;

R$^8$ is C$_1$–C$_4$ alkyl, phenyl, substituted phenyl, or di(C$_1$–C$_4$ alkyl)amino;

Y is S or O, and pharmaceutically acceptable acid addition salts thereof.

A further embodiment of this invention are novel optionally substituted N-[2-substituted-3-(2-aminoethyl)-1H-indol-5-yl]amides of Formula II:

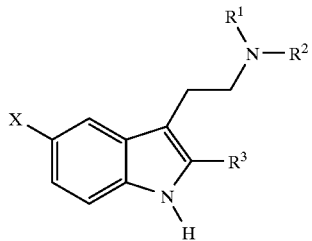

II in which

R$^1$ is hydrogen or C$_1$–C$_4$ alkyl;

R$^2$ is C$_1$–C$_4$ alkyl, C$_3$–C$_8$ cycloalkyl, cycloalkyl-(C$_1$–C$_3$ alkylene), aryl-(C$_1$–C$_3$ alkylene), or heteroaryl-(C$_1$–C$_3$ alkylene);

R$^3$ is hydrogen or C$_1$–C$_4$ alkyl;

X is R$^4$C(O)NH—, R$^5$R$^6$NC(Y)NH—, R$^7$OC(O)NH—, or R$^8$SO$_2$NH—;

R$^4$ is C$_1$–C$_4$ alkyl, C$_3$–C$_7$ cycloalkyl, phenyl, substituted phenyl, biphenylyl, naphthyl, or a heterocycle;

R$^5$ and R$^6$ are independently selected from the group consisting of hydrogen, C$_1$–C$_6$ alkyl, C$_3$–C$_6$ alkenyl, C$_3$–C$_8$ cycloalkyl, phenyl, substituted phenyl, phenyl (C$_1$–C$_4$ alkylene), phenyl(C$_1$–C$_4$ alkylene) substituted in the phenyl ring, ((C$_1$–C$_4$ alkyl or C$_1$–C$_4$ alkoxycarbonyl substituted)C$_1$–C$_4$ alkyl)phenyl, C$_1$–C$_4$ alkyl α-substituted with C$_1$–C$_4$ alkoxycarbonyl; or R$^5$ and R$^6$ taken together with the nitrogen atom to which they are attached form a pyrrolidine, piperidine, piperazine, 4-substituted piperazine, morpholine or thiomorpholine ring;

R$^7$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;

$R^8$ is $C_1$–$C_4$ alkyl, phenyl, substituted phenyl, or di($C_1$–$C_4$ alkyl)amino;

Y is S or O, and pharmaceutically acceptable acid addition salts thereof subject to the following provisos:

1) $R^1$ and $R^3$ may be hydrogen only when $R^2$ is heteroaryl ($C_1$–$C_4$ alkylene); and
2) X may be $R^5R^6NC(Y)NH$—, $R^7OC(O)NH$—, or $R^8SO_2NH$— only when $R^2$ is heteroaryl($C_1$–$C_4$ alkylene).

This invention also provides a pharmaceutical formulation which comprises, in association with a pharmaceutically acceptable carrier, diluent or excipient, a compound of Formula II.

A further embodiment of this invention is a method for increasing activation of the 5-$HT_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, allergic rhinitis, cold symptoms, trichotillomania, trigeminal neuralgia, dental pain or temperomandibular joint dysfunction pain. The compounds of this invention are also useful as a prophylactic treatment for migraine. Any of these methods employ a compound of Formula I.

The use of a compound of Formula I for the activation of the 5-$HT_{1F}$ receptor, for the inhibition or peptide extravasation in general or due to stimulation of the trigeminal ganglia specifically, and for the treatment of any of the disorders described supra, are all embodiments of the present invention.

This invention also provides the use of a compound of Formula II for the manufacture of a medicament for the prevention or treatment of migraine and associated disorders. Additionally, this invention provides a pharmaceutical formulation adapted for the prevention or treatment of migraine containing a compound of Formula II. Furthermore, this invention includes a method for the prevention or treatment of migraine which comprises administering an effective amount of a compound of Formula II.

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, and the like. The term "cycloalkyl" includes cyclopropyl, cyclobutyl, cyclopentyl, cyclohexyl, and cycloheptyl. The term "acyl" includes formyl, acetyl, propanoyl, butanoyl, and 2-methylpropanoyl. The term "($C_1$–$C_4$ alkyl)sulfonyl" includes methanesulfonyl, ethanesulfonyl, propanesulfonyl, isopropanesulfonyl, butanesulfonyl and the like. The term "halogen" includes fluoro, chloro, bromo and iodo.

The term "substituted phenyl" is taken to mean a phenyl ring substituted with 1 to 3 substitutents independently selected from the group consisting of halogen, $C_1$–$C_4$ alkoxy, $C_1$–$C_4$ alkylthio, $C_1$–$C_4$ alkyl, $C_1$–$C_4$ alkylsulfonyl, nitro, trifluoromethyl, N—($C_1$–$C_4$ acyl)amino, N—($C_1$–$C_4$ alkyl)-N—($C_1$–$C_4$ acyl)amino, N,N-di($C_1$–$C_4$ alkyl)amino and $C_1$–$C_4$ alkoxycarbonyl.

The term "heterocycle" is taken to mean a thienyl, benzothienyl, furyl, benzofuryl, isobenzofuryl, pyrrolyl, 1-($C_1$–$C_3$ alkyl)pyrrolyl, imidazolyl, pyrazolyl, 1-($C_1$–$C_3$ alkyl)pyrazolyl, pyridyl, pyrazinyl, pyrimidinyl, pyridazinyl, indolyl, indazolyl, quinolinyl, isoquinolinyl, quinoxalinyl, thiazolyl, benzothiazolyl, oxazolyl, benzoxazolyl, 1,3-benzodioxolyl, 1,4-benzodioxanyl, isoxazolyl, benzisoxazolyl, oxadiazolyl or triazolyl bonded through any available ring carbon atom. Each of these rings may be substituted on available ring carbon atoms with up to two substituents independently selected from the group consisting of halo, hydroxy, $C_1$–$C_4$ alkyl, $C_1$–$C_4$ alkoxy, $C_1$–$C_4$ alkylthio, hydroxy substituted ($C_1$–$C_4$ alkylene), cyano, carboxamido, nitro, amino, or di($C_1$–$C_4$ alkyl)amino.

The term "cycloalkyl-($C_1$–$C_3$ alkylene)" is taken to be an alkylene chain of 1–3 carbon atoms which may be mono-substituted with a methyl group and to which is bonded a $C_3$–$C_8$ cycloalkyl moiety.

The term "aryl-($C_1$–$C_3$ alkylene)" is taken to be an alkylene chain of 1–3 carbon atoms which may be mono-substituted with a methyl group and to which is bonded a phenyl or substituted phenyl moiety.

The term "heteroaryl-($C_1$–$C_3$ alkylene)" is taken to be an alkylene chain of 1–3 carbon atoms optionally monosubstituted with a methyl group and to which is bonded a heterocycle.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl($C_1$–$C_4$ alkylene) substituted in the phenyl ring, heteroaryl, and heteroaryl ($C_1$–$C_4$ alkylene).

While all of the compounds of this invention are useful as 5-$HT_{1F}$ agonists, certain classes are preferred. The following paragraphs describe such preferred classes.

aa) $R^1$ is methyl;
ab) $R^2$ is $C_1$–$C_4$ alkyl;
ac) $R^2$ is methyl;
ad) $R^2$ is ethyl;
ae) $R^2$ is aryl-($C_1$–$C_3$ alkylene);
af) $R^2$ is 1-phenyl-1-ethyl;
ag) $R^2$ is 2-phenylethyl;
ah) $R^2$ is heteroaryl-($C_1$–$C_3$ alkylene);
ai) $R^2$ is 2-(1-($C_1$–$C_4$ alkyl)pyrazol-4-yl)ethyl;
aj) $R^2$ is (pyridin-2-yl)methyl;
ak) $R^2$ is 3-thienylmethyl;
al) $R^2$ is 3-indolylmethyl;
am) $R^2$ is 2-thienylmethyl;
an) $R^2$ is 2-furylmethyl;
ao) $R^2$ is (5-methylfur-2-yl)methyl;
ap) $R^2$ is (1-methylpyrrol-2-yl)methyl;
aq) $R^2$ is (5-hydroxymethylfur-2-yl)methyl;
ar) $R^2$ is (6-chloro-1,3-benzodioxol-5-yl)methyl;
as) $R^2$ is (3-methylbenzothien-2-yl)methyl;
at) $R^2$ is cycloalkyl-($C_1$–$C_3$ alkylene);
au) $R^3$ is hydrogen;
av) $R^3$ is $C_1$–$C_4$ alkyl;
aw) $R^3$ is methyl;
ax) X is $R^4C(O)NH$—;
ay) X is $R^5R^6NC(Y)NH$—;
az) X is $R^7OC(O)NH$—;
ba) X is $R^8SO_2NH$—;
bb) $R^4$ is $C_1$–$C_4$ alkyl;
bc) $R^4$ is $C_3$–$C_7$ cycloalkyl;
bd) $R^4$ is substituted phenyl;
be) $R^4$ is phenyl;
bf) $R^4$ is phenyl monosubstituted with halogen;
bg) $R^4$ is 4-fluorophenyl;

bh) $R^4$ is phenyl disubstituted with halogen;
bi) $R^4$ is phenyl 2,6-disubstituted with halogen;
bj) $R^4$ is phenyl 2,4-disubstituted with halogen;
bk) $R^4$ is 2-chloro-4-fluorophenyl;
bl) $R^4$ is phenyl trisubstituted with halogen;
bm) $R^4$ is phenyl 2,4,6-trisubstituted with halogen;
bn) $R^4$ is 2-methyl-4-fluorophenyl;
bo) $R^4$ is a heterocycle;
bp) $R^4$ is thienyl;
bq) $R^4$ is furyl;
br) $R^5$ is H;
bs) $R^6$ is $C_1$–$C_4$ alkyl;
bt) $R^6$ is methyl;
bu) $R^6$ is ethyl;
bv) $R^6$ is propyl;
bw) $R^6$ is isopropyl;
bx) $R^6$ is phenyl;
by) $R^6$ is $C_3$–$C_8$ alkenyl;
bz) $R^6$ is allyl;
ca) $R^6$ is phenyl monosubstituted with halo;
cb) $R^6$ is 4-fluorophenyl;
cc) $R^6$ is 4-chlorophenyl;
cd) $R^6$ is phenyl($C_1$–$C_4$ alkylene)
ce) $R^6$ is benzyl;
cf) $R^6$ is phenethyl;
cg) $R^5$ and $R^6$ taken together with the nitrogen to which they are attached form a morpholine ring;
ch) $R^5$ and $R^6$ taken together with the nitrogen to which they are attached form a thiomorpholine ring;
ci) $R^5$ and $R^6$ taken together with the nitrogen to which they are attached form a pyrrolidine ring;
cj) $R^5$ and $R^6$ taken together with the nitrogen to which they are attached form a piperidine ring;
ck) $R^5$ and $R^6$ taken together with the nitrogen to which they are attached form a pyrrolidine ring;
cl) $R^5$ and $R^6$ taken together with the nitrogen to which they are attached form a piperazine ring;
cm) $R^5$ and $R^6$ taken together with the nitrogen to which they are attached form a 4-substituted piperazine ring;
cn) $R^7$ is $C_1$–$C_4$ alkyl;
co) $R^7$ is methyl;
cp) $R^7$ is ethyl;
cq) $R^7$ is propyl;
cr) $R^7$ is $C_3$–$C_6$ alkenyl;
cs) $R^7$ is allyl;
ct) $R^7$ is $C_3$–$C_8$ cycloalkyl;
cu) $R^7$ is cyclopentyl;
cv) $R^7$ is phenyl monosubstituted with $C_1$–$C_4$ alkoxy;
cw) $R^7$ is 4-methoxyphenyl;
cx) $R^8$ is $C_1$–$C_4$ alkyl;
cy) $R^8$ is methyl;
cz) $R^8$ is ethyl;
da) $R^8$ is phenyl;
db) $R^8$ is di($C_1$–$C_4$ alkyl)amino;
dc) $R^8$ is dimethylamino;
dd) Y is O;
de) The compound is a free base;
df) The compound is a salt;
dg) The compound is the hydrochloride salt;
dh) The compound is the fumarate salt;
di) The compound is the oxalate salt.

It will be understood that the above classes may be combined to form additional preferred classes.

The compounds of this invention are useful in a method for increasing activation of the 5-$HT_{1F}$ receptor for treating a variety of disorders which have been linked to decreased neurotransmission of serotonin in mammals. It is preferred that the mammal to be treated by the administration of compounds of this invention is human. It is also preferred that the compounds used for the method of the invention are of Formula II.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

The following group is illustrative of compounds contemplated within the scope of this invention:

N-[2-methyl-3-(2-[N',N'-diethylamino]ethyl)-1H-indol-5-yl]-4-propanesulfonylbenzamide hydrochloride N-[2-ethyl-3-(2-[N'-methyl-N'-isopropylamino]ethyl)-1H-indol-5-yl]-3-ethylthiobenzamide hydroiodide N-[2-propyl-3-(2-[N'-ethyl-N'-cyclopentylpropylamino]ethyl)-1H-indol-5-yl]-4-ethyl-2-propoxycarbonylbenzamide hydrobromide N-[2-isopropyl-3-(2-[N',N'-dibutylamino]ethyl)-1H-indol-5-yl]-4-(N",N"-dipropylamino)benzamide oxalate N-[2-n-butyl-3-(2-[N'-methyl-N'-benzylamino]ethyl)-1H-indol-5-yl]-4-isopropylbenzamide sulfate N-[2-isobutyl-3-(2-[N'-methyl-N'-cyclopropylmethylamino]ethyl)-1H-indol-5-yl]-4-(N"-ethyl-N"-butanoyl)aminobenzamide acetate N-[2-s-butyl-3-(2-[N'-methyl-N'-(2-[1-propylpyrazol-4-yl]ethyl)amino]ethyl)-1H-indol-5-yl]-2-nitrobenzamide phosphate N-[2-t-butyl-3-(2-[N'-methyl-N'-(1-ethylpyrazol-4-ylmethyl)amino]ethyl)-1H-indol-5-yl]-4-isobutylsulfonylbenzamide malonate N-[2-methyl-3-(2-[N'-methyl-N'-isobutylamino]ethyl)-1H-indol-5-yl]-3-ethylbenzamide tartrate N-[2-methyl-3-(2-[N'-methyl-N'-(2-[pyridin-4-yl]ethyl)amino]ethyl)-1H-indol-5-yl]-3-t-butoxybenzamide citrate N-[2-methyl-3-(2-[N'-methyl-N'-s-butylamino]ethyl)-1H-indol-5-yl]-4-formylamino-2-propylbenzamide 4-toluenesulfonate N-[2-methyl-3-(2-[N'-methyl-N'-(2-[4-bromopyridin-3-yl]ethyl)amino]ethyl)-1H-indol-5-yl]-3-t-butoxybenzamide benzoate N-[2-methyl-3-(2-[N'-methyl-N'-(2-[1-isopropylpyrazol-4-yl]ethyl)amino]ethyl)-1H-indol-5-yl]-4-isopropylthiobenzamide fumarate N-[2-ethyl-3-(2-[N',N'-diethylamino]ethyl)-1H-indol-5-yl]-4-fluorobenzamide naphthalene-1-sulfonate N-[2-ethyl-3-(2-[N'-methyl-N'-isopropylamino]ethyl)-1H-indol-5-yl]-4-fluorobenzamide N-[2-propyl-3-(2-[N'-ethyl-N'-cyclopentylpropylamino]ethyl)-1H-indol-5-yl]-4-bromobenzamide phthalate N-[2-isopropyl-3-(2-[N',N'-dibutylamino]ethyl)-1H-indol-5-yl]-4-fluorobenzamide methanesulfonate N-[2-n-butyl-3-(2-[N'-methyl-N'-benzylamino]ethyl)-1H-indol-5-yl]-4-fluorobenzamide N-[2-isobutyl-3-(2-[N'-methyl-N'-cyclopropylmethylamino]ethyl)-1H-indol-5-yl]-4-iodobenzamide naphthalene-1-sulfonate N-[2-s-butyl-3-(2-[N'-methyl-N'-(2-[1-propylpyrazol-4-yl]ethyl)amino]ethyl)-1H-indol-5-yl]-4-fluorobenzamide ditoluoyltartrate N-[2-t-butyl-3-(2-[N'-methyl-N'-(1-ethylpyrazol-4-ylmethyl)amino]ethyl)-1H-indol-5-yl]-4-fluorobenzamide N-[2-methyl-3-(2-[N'-methyl-N'-isobutylamino]ethyl)-1H-indol-5-yl]-2-bromo-4-fluorobenzamide N-[2-methyl-3-(2-[N'-methyl-N'-(2-[pyridin-4-yl]ethyl)amino]ethyl)-1H-indol-5-yl]-4-fluorobenzamide N-[2-methyl-3-(2-[N'-methyl-N'-s-butylamino]ethyl)-1H-indol-5-yl]-isobutyramide N-[2-methyl-3-(2-[N'-methyl-N'-(2-[pyridin-4-yl]ethyl)amino]ethyl)-1H-indol-5-yl]-4-fluorobenzamide malonate N-[2-methyl-3-(2-[N'-methyl-N'-(2-[1-isopropylpyrazol-4-yl]ethyl)amino]ethyl)-1H-indol-5-yl]-butyramide mandelate N-[3-(2-[N'-methyl-N'-([4-bromothien-2-yl]methyl)amino]ethyl)-1H-indol-5-yl]-4-fluorobenzamide hydrochloride N-[2-ethyl-3-(2-[N'-ethyl-N'-(2-[3-methylthiobenzofur-5-yl]ethyl)amino]ethyl)-1H-indol-5-yl]pyridine-2-carboxamide N-[2-propyl-3-(2-[N'-isopropyl-N'-(3-[isobenzofur-2-yl]propyl)amino]ethyl)-1H-indol-5-yl]-4-fluorobenzamide N-[2-methyl-3-(2-[N'-butyl-N'-([pyrrol-3-yl]methyl)amino]ethyl)-1H-indol-5-yl]-4-fluorobenzamide maleate N-[2-methyl-3-(2-[N'-methyl-N'-([5-cyanoimidazol-2-yl]methyl)amino]ethyl)-1H-indol-5-yl]acetamide trifluoroacetate N-[2-methyl-3-(2-[N'-methyl-N'-([6-carboxamidopyrazin-2-yl]methyl)amino]ethyl)-1H-indol-5-yl]propanamide N-[2-methyl-3-(2-[N'-methyl-N'-([5-nitropyrimidin-2-yl]methyl)amino]ethyl)-1H-indol-5-yl]-2-propanamide N-[2-methyl-3-(2-[N'-methyl-N'-((5-dimethylaminopyridazin-3-yl]methyl)amino]ethyl)-1H-indol-5-yl]butyramide benzoate N-[2-methyl-3-(2-[N'-methyl-N'-([indazol-5-yl]methyl)amino]ethyl)-1H-indol-5-yl]pentanamide N-[2-methyl-3-(2-[N'-methyl-N'-([quinolin-4-yl]methyl)amino]ethyl)-1H-indol-5-yl]cyclopropanecarboxamide N-[2-methyl-3-(2-[N'-methyl-N'-([isoquinolin-7-yl]methyl)amino]ethyl)-1H-indol-5-yl]cyclobutanecarboxamide N-[2-methyl-3-(2-[N'-methyl-N'-([quinoxalin-2-yl]methyl)amino]ethyl)-1H-indol-5-yl]cyclopentanecarboxamide hexanoate N-[2-methyl-3-(2-[N'-methyl-N'-([quinazolin-5-yl]methyl)amino]ethyl)-1H-indol-5-yl]cyclohexanecarboxamide N-[2-methyl-3-(2-[N'-methyl-N'-([thiazol-2-yl]methyl)amino]ethyl)-1H-indol-5-yl]cycloheptanecarboxamide N-[2-methyl-3-(2-[N'-methyl-N'-([2-aminobenzothiazol-5-yl]methyl)amino]ethyl)-1H-indol-5-yl]-4-fluorobenzamide trifluoromethanesulfonate N-[2-methyl-3-(2-[N'-methyl-N'-([oxazol-5-yl]methyl)amino]ethyl)-1H-indol-5-yl]-3-iodobenzamide N-[2-methyl-3-(2-[N'-methyl-N'-([6-nitrobenzoxazol-2-yl]methyl)amino]ethyl)-1H-indol-5-yl]-2-chlorobenzamide hydrobromide N-[2-methyl-3-(2-[N'-methyl-N'-([1,4-benzodioxan-6-yl]methyl)amino]ethyl)-1H-indol-5-yl]-2-chloropyridine-3-carboxamide N-[2-isopropyl-3-(2-[N'-methyl-N'-([isoxazol-4-yl]methyl)amino]ethyl)-1H-indol-5-yl]benzamide N-[2-methyl-3-(2-[N'-methyl-N'-([benzisoxazol-3-yl]methyl)amino]ethyl)-1H-indol-5-yl]thiophene-2-carboxamide N-[2-methyl-3-(2-[N'-methyl-N'-([1,3,4-oxadiazol-2-yl]methyl)amino]ethyl)-1H-indol-5-yl]furan-3-carboxamide N-[2-methyl-3-(2-[N'-methyl-N'-([1,2,3-triazol-4-yl]methyl)amino]ethyl)-1H-indol-5-yl]-4-fluorobenzamide tosylate N-[3-(2-[N'-methyl-N'-((4-bromothien-2-yl)methyl)amino]ethyl)-1H-indol-5-yl)]-4-fluorobenzamide hydrochloride N-[2-ethyl-3-(2-[N'-ethyl-N'-((3-methylthiobenzofur-5-yl)ethyl)amino]ethyl)-1H-indol-5-yl]pyridine-2-carboxamide N-[2-propyl-3-(2-[N'-isopropyl-N'-1-((isobenzofur-2-yl)prop-3-yl)amino]ethyl)-1H-indol-5-yl]-4-fluorobenzamide N-[2-methyl-3-(2-[N'-butyl-N'-(pyrrol-3-yl)methyl)amino]ethyl)-1H-indol-5-yl]-4-fluorobenzamide maleate N-[2-methyl-3-(2-[N'-methyl-N'-((5-cyanoimidazol-2-yl(methyl)amino]ethyl)-1H-indol-5-yl]-4-acetamide trifluoroacetate N-[2-methyl-3-(2-[N'-methyl-N'-((6-carboxamidopyrazin-2-yl)methyl)amino]ethyl)-1H-indol-5-yl]propanamide N-[2-methyl-3-(2-[N'-methyl-N'-((5-nitropyrimidin-2-yl)methyl)amino]ethyl)-1H-indol-5-yl]-2-propanamide N-[2-methyl-3-(2-[N'-methyl-N'-((5-dimethylaminopyridazin-3-yl)methyl)amino]ethyl)-1H-indol-5-yl]butyramide benzoate N-[2-methyl-3-(2-[N'-methyl-N'-((indazol-5-yl)methyl)amino]ethyl)-1H-indol-5-yl]pentanamide N-[2-methyl-3-(2-[N'-methyl-N'-((quinolin-4-yl)methyl)amino]ethyl)-1H-indol-5-yl]cyclopropanecarboxamide N-[2-methyl-3-(2-[N'-methyl-N'-((isoquinolin-7-yl)methyl)amino]ethyl)-1H-indol-5-yl]cyclobutanecarboxamide N-[2-methyl-3-(2-[N'-methyl-N'-((quinoxalin-2-yl)methyl)amino]ethyl)-1H-indol-5-yl]cyclopentanecarboxamide acetate N-[2-methyl-3-(2-[N'-methyl-N'-((quinazolin-5-yl)methyl)amino]ethyl)-1H-indol-5-yl]cyclohexanecarboxamide N-[2-methyl-3-(2-[N'-methyl-N'-((thiazol-2-yl)methyl)amino]ethyl)-1H-indol-5-yl]cycloheptanecarboxamide N-[2-methyl-3-(2-[N'-methyl-N'-((2-aminobenzothiazol-5-yl)methyl)amino]ethyl)-1H-indol-5-yl]-4-fluorobenzamide trifluoromethanesulfonate N-[2-methyl-3-(2-[N'-methyl-N'-(2-[pyridin-4-yl]ethyl)amino]ethyl)-1H-indol-5-yl]-N''-ethylurea N-[2-methyl-3-(2-[N'-methyl-N'-s-butylamino]ethyl)-1H-indol-5-yl]-N''-isopropylurea N-[2-methyl-3-(2-[N'-methyl-N'-(2-[pyridin-4-yl]ethyl)amino]ethyl)-1H-indol-5-yl]-N''-[(3-methoxy)phenyl]urea malonate N-[3-(2-[N'-(2-[1-isopropylpyrazol-4-yl]ethyl)amino]ethyl)-1H-indol-5-yl]-N''-[(2-ethoxy)phenyl]urea mandelate N-[3-(2-[N'-methyl-N'-([4-bromothien-2-yl]methyl)amino]ethyl)-1H-indol-5-yl]-N''-[(4-isopropoxy)phenyl]urea hydrochloride N-[2-ethyl-3-(2-[N'-(2-[3-methylthiobenzofur-5-yl]ethyl) amino]ethyl)-1H-indol-5-yl]-N"-[2,3-dibromophenyl] urea N-[2-propyl-3-(2-[N'-isopropyl-N'-(3-[isobenzofur-2-yl] propyl)amino]ethyl)-1H-indol-5-yl]-N"-[(2-bromo-3-iodo)phenyl]urea N-[2-methyl-3-(2-[N'-butyl-N'-([pyrrol-3-yl]methyl)amino] ethyl)-1H-indol-5-yl]-N"-benzylurea maleate N-[2-methyl-3-(2-[N'-methyl-N'-([5-cyanoimidazol-2-yl] methyl)amino]ethyl)-1H-indol-5-yl]-N"-phenethylurea trifluoroacetate N-[2-methyl-3-(2-[N'-methyl-N'-([6-carboxamidopyrazin-2-yl]methyl)amino]ethyl)-1H-indol-5-yl]-N"-[4-phenbutyl]urea N-[2-methyl-3-(2-[N'-methyl-N'-([5-nitropyrimidin-2-yl] methyl)amino]ethyl)-1H-indol-5-yl]-N"-[(2-trifluoromethyl)phenyl]urea N-[2-methyl-3-(2-[N'-methyl-N'-([5-dimethylaminopyridazin-3-yl]methyl)amino]ethyl)-1H-indol-5-yl]-N"-[(3-phenyl)phenyl]urea benzoate 1-{[2-methyl-3-(2-[N'-methyl-N'-([indazol-5-yl]methyl) amino]ethyl)-1H-indol-5-yl]carbonyl}pyrrolidine 1-{[2-methyl-3-(2-[N'-methyl-N'-([quinolin-4-yl]methyl) amino]ethyl)-1H-indol-5-yl]carbonyl}piperidine 1-{[2-methyl-3-(2-[N'-methyl-N'-([isoquinolin-7-yl] methyl)amino]ethyl)-1H-indol-5-yl]carbonyl}piperazine 1-{[2-methyl-3-(2-[N'-methyl-N'-([quinoxalin-2-yl]methyl) amino]ethyl)-1H-indol-5-yl]carbonyl}-4-methylpiperazine hexanoate 1-{[2-isopropyl-3-(2-[N'-methyl-N'([quinazolin-5-yl] methyl)amino]ethyl)-1H-indol-5-yl]carbonyl}-4-phenylpiperazine 1-{[3-(2-[N'-([thiazol-2-yl]methyl)amino]ethyl)-1H-indol-5-yl]carbonyl}-4-benzylpiperazine 1-{[2-methyl-3-(2-[N'-([2-aminobenzothiazol-5-yl]methyl) amino]ethyl)-1H-indol-5-yl]carbonyl}-4-(2,4-dichlorophenyl)piperazine trifluoromethanesulfonate 1-{[3-(2-[N'-methyl-N'-([oxazol-5-yl]methyl)amino]ethyl)-1H-indol-5-yl]carbonyl}morpholine 1-{[2-methyl-3-(2-[N'-methyl-N'-([6-nitrobenzoxazol-2-yl] methyl)amino]ethyl)-1H-indol-5-yl] carbonyl}thiomorpholine hydrobromide N-[2-methyl-3-(2-[N'-methyl-N'-(2-[pyridin-4-yl]ethyl) amino]ethyl)-1H-indol-5-yl]-N"'-ethylthiourea N-[2-methyl-3-(2-[N'-methyl-N'-s-butylamino]ethyl)-1H-indol-5-yl]-N"-isopropylthiourea N-[2-methyl-3-(2-[N'-methyl-N'-(2-[pyridin-4-yl]ethyl) amino]ethyl)-1H-indol-5-yl]-N"-[(3-methoxy)phenyl] thiourea malonate N-[2-methyl-3-(2-[N'-methyl-N'-(2-[1-isopropylpyrazol-4-yl]ethyl)amino]ethyl)-1H-indol-5-yl]-N"-[(2-ethoxy) phenyl]thiourea mandelate N-[2-phenyl-3-(2-[N'-methyl-N'-([4-bromothien-2-yl] methyl)amino]ethyl)-1H-indol-5-yl]-N"-[(4-isopropoxy) phenyl]thiourea hydrochloride N-[2-ethyl-3-(2-[N'-ethyl-N'-(2-[3-methylthiobenzofur-5-yl]ethyl)amino]ethyl)-1H-indol-5-yl]-N"-[2,3-dibromophenyl]thiourea N-[2-propyl-3-(2-[N'-isopropyl-N'-(3-[isobenzofur-2-yl] propyl)amino]ethyl)-1H-indol-5-yl]-N"-[(2-bromo-3-iodo)phenyl]thiourea N-[3-(2-[N'-([pyrrol-3-yl]methyl)amino]ethyl)-1H-indol-5-yl]-N"-benzylthiourea maleate N-[3-(2-[N'-methyl-N'-([5-cyanoimidazol-2-yl]methyl) amino]ethyl)-1H-indol-5-yl]-N"-phenethylthiourea trifluoroacetate N-[2-methyl-3-(2-[N'-([6-carboxamidopyrazin-2-yl]methyl) amino]ethyl)-1H-indol-5-yl]-N"-[4-phenbutyl]thiourea N-[2-methyl-3-(2-[N'-methyl-N'-([5-nitropyrimidin-2-yl] methyl)amino]ethyl)-1H-indol-5-yl]-N"-[(2-trifluoromethyl)phenyl]thiourea N-[2-methyl-3-(2-[N'-methyl-N'-([5-dimethylaminopyridazin-3-yl]methyl)amino]ethyl)-1H-indol-5-yl]-N"-[(3-phenyl)phenyl]thiourea benzoate 1-{N-[2-methyl-3-(2-[N'-methyl-N'-([indazol-5-yl]methyl) amino]ethyl)-1H-indol-5-yl] aminothiocarbonyl}pyrrolidine 1-{N-[2-methyl-3-(2-[N'-methyl-N'-([quinolin-4-yl]methyl) amino]ethyl)-1H-indol-5-yl] aminothiocarbonyl}piperidine 1-{N-[2-methyl-3-(2-[N'-methyl-N'-([isoquinolin-7-yl] methyl)amino]ethyl)-1H-indol-5-yl] aminothiocarbonyl}piperazine 1-{N-[2-methyl-3-(2-[N'-([quinoxalin-2-yl]methyl)amino] ethyl)-1H-indol-5-yl]aminothiocarbonyl}-4-methylpiperazine hexanoate 1-{N-[2-methyl-3-(2-[N'-methyl-N'-([quinazolin-5-yl] methyl)amino]ethyl)-1H-indol-5-yl]aminothiocarbonyl}-4-phenylpiperazine 1-{N-[2-methyl-3-(2-[N'-methyl-N'-([thiazol-2-yl]methyl) amino]ethyl)-1H-indol-5-yl]aminothiocarbonyl}-4-benzylpiperazine 1-{N-[2-methyl-3-(2-[N'-methyl-N'-([2-aminobenzothiazol-5-yl]methyl)amino]ethyl)-1H-indol-5-yl] aminothiocarbonyl}-4-(2,4-dichlorophenyl)piperazine trifluoromethanesulfonate 1-{N-[2-methyl-3-(2-[N'-methyl-N'-([oxazol-5-yl]methyl) amino]ethyl)-1H-indol-5-yl] aminothiocarbonyl}morpholine 1-{N-[2-methyl-3-(2-[N'-methyl-N'-([6-nitrobenzoxazol-2-yl]methyl)amino]ethyl)-1H-indol-5-yl] aminothiocarbonyl}thiomorpholine hydrobromide N-[2-methyl-3-(2-[N'-([benzisoxazol-3-yl]methyl)amino] ethyl)-1H-indol-5-yl]thiophene-2-carboxamide N-[2-methyl-3-(2-[N'-([1,3,4-oxadiazol-2-yl]methyl)amino] ethyl)-1H-indol-5-yl]furan-3-carboxamide N-[2-methyl-3-(2-[N'-([1,2,3-triazol-4-yl]methyl)amino] ethyl)-1H-indol-5-yl]-4-fluorobenzamide tosylate N-[2-phenyl-3-(2-[N'-((4-bromothien-2-yl)methyl)amino] ethyl)-1H-indol-5-yl)]-4-fluorobenzamide hydrochloride N-[2-ethyl-3-(2-[N'-((3-methylthiobenzofur-5-yl)ethyl) amino]ethyl)-1H-indol-5-yl]pyridine-2-carboxamide N-[2-propyl-3-(2-[N'-1-((isobenzofur-2-yl)prop-3-yl) amino]ethyl)-1H-indol-5-yl]-4-fluorobenzamide N-[2-methyl-3-(2-[N'-(pyrrol-3-yl)methyl)amino]ethyl)-1H-indol-5-yl]-4-fluorobenzamide maleate N-[2-methyl-3-(2-[N'-((5-cyanoimidazol-2-yl)methyl) amino]ethyl)-1H-indol-5-yl]-4-acetamide trifluoroacetate N-[2-methyl-3-(2-[N'-((6-carboxamidopyrazin-2-yl)methyl) amino]ethyl)-1H-indol-5-yl]propanamide 5-(N,N-dibutylaminosulfonyl)amino-2-methyl-3-(2-[N'-methyl-N'-((5-nitropyrimidin-2-yl)methyl)amino]ethyl)-1H-indole 5-((N-isopropyl-N-butylamino)sulfonyl)amino-2-methyl-3-(2-[N'-methyl-N'-((5-dimethylaminopyridazin-3-yl) methyl)amino]ethyl)-1H-indole benzoate 5-(dimethylaminosulfonyl)amino-2-methyl-3-(2-[N'-methyl-N'-((indazol-5-yl)methyl)amino]ethyl)-1H-indole N-[2-methyl-3-(2-[N'-methyl-N'-((quinolin-4-yl)methyl) amino]ethyl)-1H-indol-5-yl]-4-chlorophenylsulfonamide N-[2-methyl-3-(2-[N'-methyl-N'-((isoquinolin-7-yl)methyl) amino]ethyl)-1H-indol-5-yl]phenylsulfonamide N-[2-methyl-3-(2-[N'-methyl-N'-((quinoxalin-2-yl)methyl) amino]ethyl)-1H-indol-5-yl]butanesulfonamide acetate N-[2-methyl-3-(2-[N'-methyl-N'-((quinazolin-5-yl)methyl) amino]ethyl)-1H-indol-5-yl]isopropanesulfonamide N-[2-methyl-3-(2-[N'-methyl-N'-((thiazol-2-yl)methyl) amino]ethyl)-1H-indol-5-yl]propanesulfonamide N-[2-methyl-3-(2-[N'-((2-aminobenzothiazol-5-yl)methyl) amino]ethyl)-1H-indol-5-yl]ethanesulfonamide trifluoromethanesulfonate 5-isopropoxycarbonylamino-2-methyl-3-(2-[N'-methyl-N'-(2-[1-isopropylpyrazol-4-yl]ethyl)amino]ethyl)-1H-indole mandelate 5-methoxycarbonylamino-(2-[N'-methyl-N'-([4-bromothien-2-yl]methyl)amino]ethyl)-1H-indole hydrochloride 5-(tert-butoxycarbonyl)amino-2-ethyl-3-(2-[N'-ethyl-N'-(2-[3-methylthiobenzofur-5-yl]ethyl)amino]ethyl)-1H-indole 5-(1-penten-5-yloxy)carbonylamino-2-propyl-3-(2-[N'-isopropyl-N'-(3-[isobenzofur-2-yl]propyl)amino]ethyl)-1H-indole 5-(1-buten-4-yloxy)carbonylamino-2-methyl-3-(2-[N'-butyl-N'-([pyrrol-3-yl]methyl)amino]ethyl)-1H-indole maleate 5-(4-hexen-6-yloxy)carbonylamino-3-(2-[N'-methyl-N'-([5-cyanoimidazol-2-yl]methyl)amino]ethyl)-1H-indole trifluoroacetate 5-(2-chlorophenoxy)carbonylamino-2-methyl-3-(2-[N'-([6-carboxamidopyrazin-2-yl]methyl)amino]ethyl)-1H-indole 5-(3-bromophenoxy)carbonylamino-3-(2-[N'-(]5-nitropyrimidin-2-yl]methyl)amino]ethyl)-1H-indole 5-(3-methoxyphenoxy)carbonylamino-2-methyl-3-(2-[N'-methyl-N'-(]5-dimethylaminopyridazin-3-yl]methyl) amino]ethyl)-1H-indole benzoate 5-cyclopropoxycarbonylamino-2-methyl-3-(2-[N'-methyl-N'-([indazol-5-yl]methyl)amino]ethyl)-1H-indole 5-cyclohexyloxycarbonylamino-2-methyl-3-(2-[N'-methyl-N'-([quinolin-4-yl]methyl)amino]ethyl)-1H-indole 5-cyclooctyloxycarbonylamino-2-methyl-3-(2-[N'-methyl-N'-([isoquinolin-7-yl]methyl)amino]ethyl)-1H-indole 5-(butoxymethoxy)carbonylamino-2-methyl-3-(2-[N'-methyl-N'-([quinoxalin-2-yl]methyl)amino]ethyl)-1H-indole hexanoate 5-(ethoxypropoxy)carbonylamino-N-[2-methyl-3-(2-[N'-methyl-N'-([quinazolin-5-yl]methyl)amino]ethyl)-1H-indole The synthetic methodology required to prepare the compounds of the invention is well known to those skilled in the art. An appropriate nitrobenzene is hydrogenated to give the corresponding aniline. This aniline is then diazotized and reduced to give the corresponding hydrazine which is then combined with an appropriate ketone under Fischer indole cyclization conditions to give the compounds of the present invention. This chemistry is illustrated in Synthetic Scheme I where X is $R^4C(O)NH-$, $R^5R^6NC(Y)NH-$, or $R^8SO_2NH-$ and $R^1$, $R^2$, $R^3$, $R^4$, $R^5$, $R^6$, $R^8$ and Y are as described supra.

Synthetic Scheme I

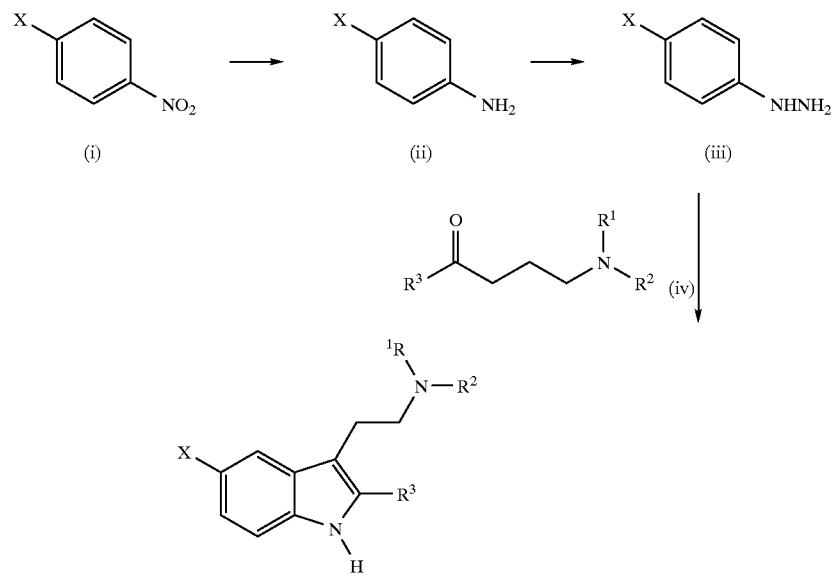

The 4-nitrobenzenes (i) are converted to the corresponding 4-aminobenzenes (ii) by catalytic hydrogenation. These hydrogenations are performed using a precious metal catalyst, such as platinum oxide or platinum or palladium on a support such as carbon. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The 4-aminobenzenes (ii) prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

The 4-aminobenzenes (ii) are then diazotized by suspension in concentrated hydrochloric acid cooled to about 0° C. To this cooled mixture is then added an aqueous solution of sodium or potassium nitrite at such a rate as to maintain the temperature of the reaction mixture at or below 5° C. The reaction is stirred at about 0° C. for from about 10 minutes to about an hour. The resulting diazonium salt mixture is reduced directly by dropwise addition to a solution of stannous chloride in concentrated hydrochloric acid at such a rate as to maintain the temperature of the reaction mixture at about 0° C. A solid forms which is recovered by filtration. The solid is partitioned between an aqueous base, such as sodium hydroxide, and a suitable water immiscible solvent, such as diethyl ether or ethyl acetate. The hydrazine (iii) is isolated by separating the water immiscible phase, drying over an appropriate dessicant, such as sodium or magnesium sulfate, and removing the solvent under reduced pressure. The product recovered may be used directly in a subsequent step or further purified by chromatography, or by recrystallization from a suitable solvent.

The hydrazines (iii) are then reacted with an appropriate aminoketone (iv) under standard Fischer indolization conditions as described in Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985), to provide the compounds of the present invention.

The nitrobenzenes required for the synthesis of the compounds of the present invention may be prepared by reacting suitable electrophiles with 4-nitroaniline to provide the corresponding ureas, thioureas, sulfonamides and carboxamides. This chemistry is illustrated in Synthetic Scheme II where $R^4$, $R^5$, $R^6$, and $R^8$ are as described supra.

Synthetic Scheme II

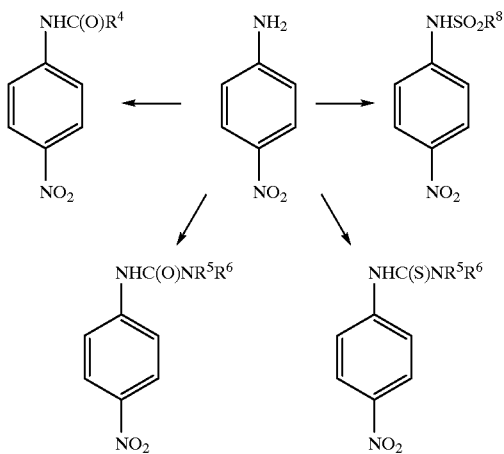

To prepare compounds of the invention where X is $R^8SO_2NH$—, a solution of 4-nitroaniline in a suitable solvent, such as tetrahydrofuran, dioxane, diethyl ether or dimethylformamide, at a temperature from about ambient to about 0° C., is reacted with a commercially available $R^8$-sulfonyl halide or $R^8$-sulfonic anhydride in the presence of a suitable base such as pyridine or triethylamine. The resultant sulfonamide may be isolated by dilution of the reaction mixture with water, adjustment of pH, and extraction with a water immiscible solvent such as dichloromethane. The product may be used for further reaction as recovered, or may be purified by chromatography, or by recrystallization from a suitable solvent.

Compounds of the invention where X is —NHC(Y)$NR^5R^6$ are prepared by treating a solution of nitroaniline in a suitable solvent, such as chloroform or dichloromethane, with an appropriate isocyanate, isothiocyanate, carbamoyl chloride or carbamoyl bromide. Appropriate carbamoyl chlorides are available by treating an amine of formula HNR$^5$R$^6$ with phosgene. When a carbamoyl chloride or carbamoyl bromide is used, the reactions are performed in the presence of a suitable base. Suitable bases include amines typically used as acid scavengers, such as pyridine or triethylamine, or commercially available polymer bound bases such as polyvinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds of the invention which are ureas may be converted into the corresponding thiourea by treatment with [2,4-bis(4-methoxyphenyl)-1,3-dithia-2,4-diphosphetane-2,4-disulfide] (Lawesson's Reagent) or phosphorus pentasulfide.

Compounds of the invention where X is $R^4C(O)NH$— are prepared by treating 4-nitroaniline with an appropriate carboxylic acid chloride, bromide or anhydride, optionally in the presence of an acylation catalyst such as dimethylaminopyridine, in the presence of a suitable base. Suitable bases include amines typically used as acid scavengers, such as pyridine or triethylamine, or commercially available polymer bound bases such as polyvinylpyridine. When an excess of the carboxylic acid chloride, bromide or anhydride is necessary to ensure complete reaction of the amine, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture to remove the polymer bound constituents, and then concentration of the filtrate under reduced pressure to isolate the desired product. The product from these reactions may be purified chromatographically or recrystallized from a suitable solvent if desired.

Alternatively, the 4-nitroaniline is reacted with an appropriate carboxylic acid in the presence of a typical peptide coupling reagent such as N,N'-carbonyldiimidazole (CDI), N,N'-dicyclohexylcarbodiimide (DCC) and 1-(3-dimethylaminopropyl)-3-ethylcarbodiimide hydrochloride (EDC). Polymer supported forms of carbodiimide peptide coupling reagents are useful for the preparation of compounds of the present invention. A polymer supported form of EDC, for example, has been described (*Tetrahedron Letters*, 34(48), 7685 (1993)). Additionally, a new carbodiimide coupling reagent, 1-(3-(1-pyrrolidinyl)propyl)-3-ethylcarbodiimide (PEPC), and its corresponding polymer supported forms have been discovered and are very useful for the preparation of the compounds of the present invention.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethyl-phenylacetamidomethyl resin (Pam Resin) and 4-benzyloxybenzyl alcohol resin (Wang Resin) available from Advanced Chemtech of Louisville, Ky. (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis. (see Aldrich 1994–1995 catalog, page 899).

Methods for the preparation of PEPC and its polymer supported forms are outlined in the following scheme.

Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient to about 45° C., for from about three hours to about three days. Typically, the product may be isolated by washing the reaction with water and concentrating the remaining organics under reduced pressure. As discussed supra, isolation of products from reactions where a polymer bound reagent has been used is greatly simplified, requiring only filtration of the reaction mixture and then concentration of the filtrate under reduced pressure. The N-(4-nitro)phenylamides from these reactions may be used directly in a subsequent step or first purified chromatographically or recrystallized from a suitable solvent prior to further reaction if desired.

The aminoketones required for the Fischer indolization step are available by methods well known to the skilled artisan. One method is to react an appropriate haloketone, optionally protected as the corresponding ketal, with an appropriate amine or phthalimidate salt under standard alkylating conditions as described in Synthetic Scheme III, where halo is chloro, bromo or iodo and $R^1$, $R^2$ and $R^3$ are as defined supra.

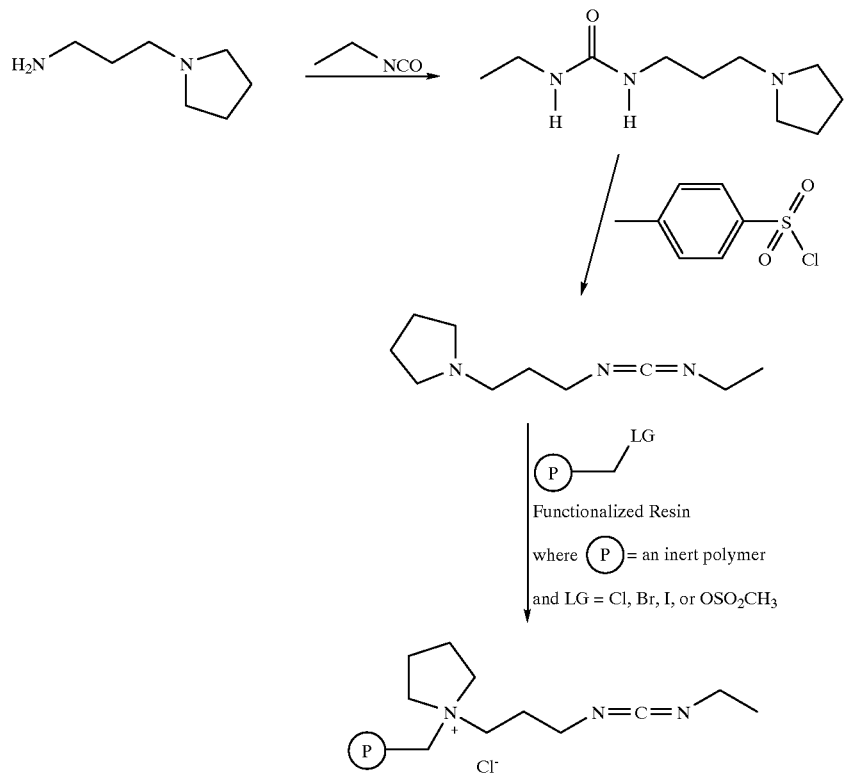

Synthetic Scheme III

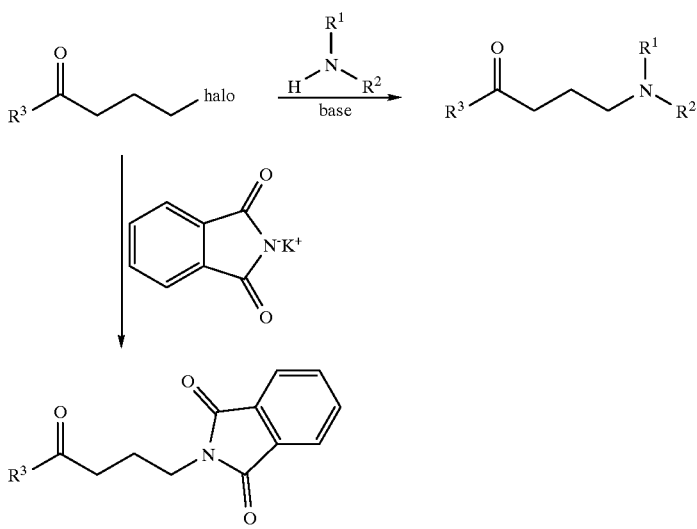

The haloketone and an appropriate amine are combined in a suitable solvent, such as acetonitrile, dichloromethane, acetone or dimethylformamide, in the presence of a suitable base, such as potassium or sodium carbonate. The skilled artisan will appreciate that when the haloketone is reacted with a phthalimidate salt, however, no additional base is required. The resulting mixture is heated to a temperature from about 40° C. to about 120° C. until all reactants are consumed. These reactions typically require about 2 hours to about 3 days to reach completion. The desired aminoketones may be isolated by filtering the reaction mixture to remove any solids which have formed, and concentrating the reaction mixture under reduced pressure. Alternatively, the reaction mixture may be partitioned between water and a water immiscible solvent such as dichloromethane. The water immiscible phase is then concentrated under reduced pressure to provide the desired compound. The aminoketones isolated in this manner may be used directly in a subsequent step or purified by distillation, chromatography, or crystallization from a suitable solvent if desired.

The skilled artisan will appreciate that certain of the compounds of the present invention, while useful as $5-HT_{1F}$ agonists in their own right, are also useful intermediates for the preparation of other compounds of the present invention. The amide moiety, for example, may be hydrolyzed to provide the corresponding 5-amino-3-(2-aminoethyl)-1H-indole. This hydrolysis may be performed by heating a mixture of the amide and 6N hydrochloric acid at reflux for about 4 hours to about 2 days. After cooling, the aqueous phase is extracted with a water immiscible solvent, such as toluene, benzene or hexane. This water immiscible phase is discarded and then the remaining aqueous phase is treated with a base such as sodium, potassium or ammonium hydroxide, until the solution has reached a pH of about 11 or 12. The aqueous phase is then extracted with a water immiscible solvent like dichloromethane. These organic extracts are concentrated under reduced pressure to give the corresponding 5-amino-3-(2-aminoethyl)-1H-indole which may be reacted directly or first purified by chromatography or recrystallization from an appropriate solvent.

Compounds of the invention where X is —NHC(O)OR$^{12}$ are prepared by reacting the 5-amino-3-(2-aminoethyl)-1H-indole with an appropriately substituted chloroformate in the presence of a suitable amine under the conditions described for Synthetic Scheme II. Likewise, the skilled artisan will appreciate that the amides, ureas, thioureas, and sulfonamides of the invention may be prepared by reacting the 5-amino-3-(2-aminoethyl)-1H-indole with an appropriate electrophile as described supra.

Alternatively, the 2-substituted-5-amino-3-(2-aminoethyl)-1H-indoles may be prepared by the reaction of 4-nitrophenylhydrazine with an appropriate aminoketone (Synthetic Scheme I) under the Fischer indolization conditions described by Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985). The resulting 5-nitroindole may be hydrogenated to give the same 2-substituted-5-amino-3-(2-aminoethyl)-1H-indoles prepared by the hydrolysis described supra.

Additionally, when compounds of the present invention where R$^2$ is benzyl or 1-phenylethyl are subjected to the hydrogenation conditions described supra, the R$^2$ substituent is removed by hydrogenolysis to give the corresponding secondary amines (III). These secondary amines may then be alkylated with an appropriate alkylating agent under the alkylation conditions described supra, or they may be subjected to reductive alkylation conditions in the presence of an appropriate aldehyde, to provide additional compounds of the invention. Furthermore, the phthalimides described supra may be treated with hydrazine to provide the primary amines (IV). These primary amines may be treated subjected to sequential reductive alkylations to provide the compounds of the present invention. This chemistry is illustrated in Synthetic Scheme IV where R$^{2'}$—CHO represents an aldehyde which, after undergoing the reductive alkylation reaction provides the moiety R$^2$, and R$^1$, R$^2$, R$^3$ and X are as defined supra.

Synthetic Scheme IV

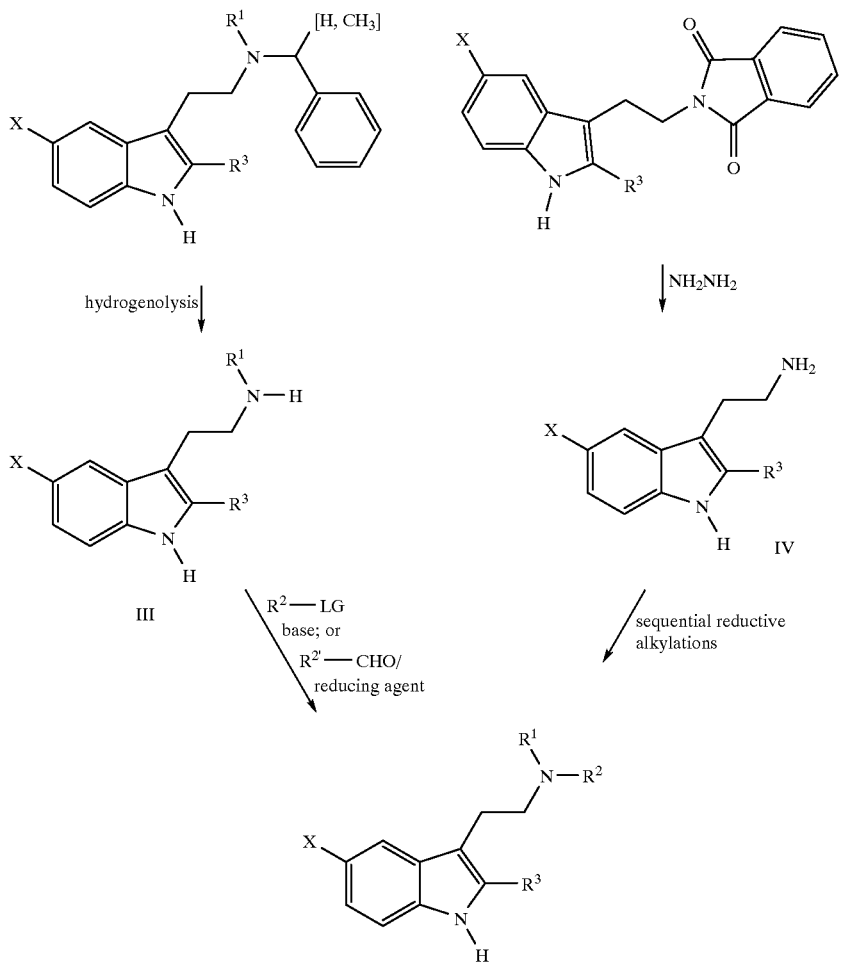

The reductive alkylation may be performed by combining an appropriate aldehyde, for example $R^{2'}$—CHO, with the secondary amine (III) or primary amine (IV) in a suitable solvent. Suitable solvents include tetrahydrofuran, dichloromethane, and the lower alkanols such as methanol, ethanol or isopropanol. The preferred solvents for the reductive alkylation include methanol and dichloromethane. The aldehyde and amine are typically combined in the presence of an acid, such as acetic acid or hydrogen chloride, and a hydride reducing agent. Suitable hydride reducing agents include sodium borohydride, sodium cyanoborohydride or sodium triacetoxyborohydride. Preferred hydride reducing agents include sodium cyanoborohydride or sodium triacetoxyborohydride. The combined reagents are allowed to react at a temperature of from about ambient to the reflux temperature of the solvent. The reaction time is typically from about 3 to about 24 hours. The compounds of the invention may then be isolated aid purified by standard extractive workups. The compounds may be further purified by chromatography or crystallization from suitable solvents if desired.

The skilled artisan will appreciate that reductive alkylations of the primary amine (IV) may be performed sequentially. One equivalent of a first aldehyde is used to prepare the corresponding secondary amine under standard reductive alkylation procedures. This secondary amine may be isolated if desired or treated directly with a second aldehyde under the reductive alkylation conditions described supra. When $R^1$ and $R^2$ are to be the same, the primary amine may be exhaustively alkylated if desired.

The skilled artisan will also appreciate that, as an alternative to the reductive alkylation conditions described supra, the aldehyde and amine may be combined in a suitable solvent in the presence of acid. The resulting imine may then be reduced in a separate step by addition of a suitable hydride reducing agent, or by subjecting the reaction mixture to hydrogenation conditions using standard precious metal catalysts. The use of hydrogenation conditions is limited to those compounds of the invention which are stable to the reaction conditions. The skilled artisan will also appreciate that while the reductive alkylation procedures described supra describe the use of aldehydes, ketones may also be used to prepare other compounds of the invention.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of this invention. The specific alkylating agent employed is determined by its commercial availability or a convenient synthesis from commercially available starting materials. The preferred alkylating agents for synthesis of compounds of this invention are those where the leaving group is chloro, bromo or methanesulfonyloxy.

Alkylating agents required to prepare compounds where $R^2$ is aryl-($C_1$–$C_3$ alkylene) or heteroaryl-($C_1$–$C_3$ alkylene), if not commercially available, are prepared from the corresponding alcohol by standard methods. When the preferred leaving group of the alkylating group is chloro, the alcohol may be treated with neat thionyl chloride at ambient temperature. When it is preferred that the leaving group for these alkylating agents is methanesulfonyloxy, they may be prepared from the corresponding alcohols as described in Synthetic Scheme V where Ar is phenyl, substituted phenyl, or a heterocycle as defined supra, and n is 1–3.

Synthetic Scheme V

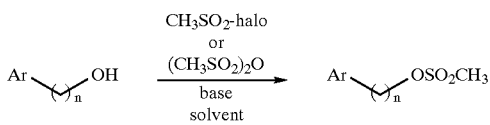

The alcohol is dissolved in a suitable anhydrous solvent such as tetrahydrofuran, diethyl ether, p-dioxane or acetonitrile which contains the base. The base must be sufficiently basic to neutralize the acid generated during the progress of the reaction but not so basic as to deprotonate other sites in the substrate giving rise to other products. Additionally, the base must not compete to any great extent with the substrate for the sulfonating reagent and must have sufficient solubility in the reaction solvent. Bases typically used in these reactions are tertiary amines such as pyridine, triethylamine or N-methylmorpholine. To the reaction mixture is then added the sulfonating reagent with cooling. The sulfonating reagent may be a methanesulfonyl halide such as the fluoride or chloride, or methanesulfonic anhydride. The reaction mixture is allowed to react from I hour to 24 hours at ambient temperature. The product is isolated by concentrating the reaction mixture under reduced pressure followed by partitioning the residue between water and an appropriate organic solvent such as dichloromethane, ethylene chloride, chloroform or carbon tetrachloride. The isolated product is used directly in the alkylation step.

The alcohols required for the synthesis of compounds of this invention where $R^2$ is aryl-($C_1$–$C_3$ alkylene) or heteroaryl-($C_1$–$C_3$ alkylene) are either commercially available or may be prepared by employing well established synthetic methodology. A general scheme for the synthesis of a number of these required alcohols is described in Synthetic Scheme VI, where Ar is pyridinyl or phenyl and n is 1–3.

Synthetic Scheme VI

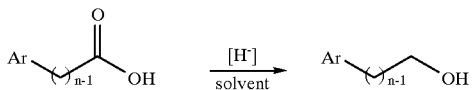

An appropriate carboxylic acid is reduced to the corresponding alcohol in diethyl ether or, preferably, tetrahydrofuran. The solution is added to a suspension of an appropriate hydride reducing agent, preferably lithium aluminum hydride, in the same solvent at reduced temperature, typically about 0° C. Once the addition is complete the mixture is allowed to warm to ambient and is stirred at ambient to reflux until the reduction is complete. The alcohol recovered may typically be used without further purification.

The starting alcohols required for the preparation of those compounds of the invention where $R^2$ is heteroaryl-($C_1$–$C_3$ alkylene) and the heteroaryl moiety is pyrazol-4-yl, may prepared by the general scheme described in Synthetic Scheme VI.

Synthetic Scheme VI

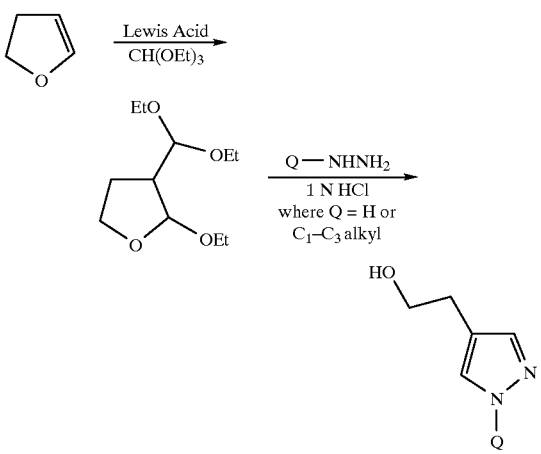

4,5-Dihydrofuran is treated with triethylorthoformate in the presence of a Lewis acid, preferably boron trifluoride diethyl etherate, for from 1 to 4 days at ambient temperature. After treating the reaction mixture with an anhydrous base such as potassium carbonate, the intermediate diacetal is distilled from the reaction mixture. This diacetal is now treated with an appropriate hydrazine in aqueous acid at reflux for 4–24 hours. The product is recovered by treatment of the reaction mixture with base and extraction of the base into methylene chloride. The alcohol so recovered is suitable for use without further purification. Where Q is H, the resulting alcohol can be further modified, if desired, by direct alkylation of one of the pyrazole nitrogens as described in Synthetic Scheme VII.

Synthetic Scheme VII

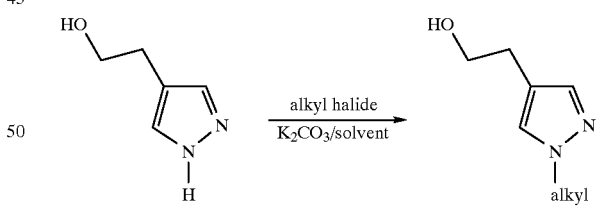

The alkylating agent is a $C_1$–$C_3$ alkyl halide, preferably the bromide or iodide. The reaction is performed under the alkylation conditions described supra.

Alternatively, the compounds of the present invention may be prepared from the appropriate 2-substituted-5-nitroindoles. These starting indoles may be prepared by reaction of 4-nitrophenylhydrazine and a ketone of formula $R^3$—C(O)$CH_3$, where $R^3$ is as defined supra, under Fischer indolization conditions as described by Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985). The 3-(2-aminoethyl) functionality may then be introduced by chemistry described by Larsen et al. (U.S. Pat. No. 3,472,870 (Oct. 14, 1969)), Smythies (U.S. Pat. No. 3,915,990 (Oct. 28, 1975)), and Stanley et al. (U.S. Pat. No. 4,803,218 (Feb. 7, 1989)), herein incorporated by reference.

The following preparations and examples further illustrate the synthesis of the compounds of this invention, and are not intended to limit the scope of the invention in any way. The compounds described below were identified by various standard analytical techniques as stated in the individual preparations and examples.

The aminoketones required for the synthesis of the compounds of the invention are available by the procedures described in Preparations I and II.

Preparation I

N,N-dimethyl-5-amino-2-pentanone

A mixture of 21.77 gm (180.5 mMol) 5-chloro-2-pentanone, 13.40 gm (164.3 mMol) dimethylamine hydrochloride and 50.0 gm (361.8 mMol) potassium carbonate in 150 mL acetonitrile was stirred at room temperature for 2 days and then at reflux for 2 hours. The reaction mixture was then cooled to room temperature and partitioned between water and dichloromethane. The phases were separated and the aqueous phase again extracted with dichloromethane. All organic phases were combined, dried over sodium sulfate and concentrated under reduced pressure. The residue was subjected to silica gel chromatography, eluting with dichloromethane containing 10% methanol and 1% ammonium hydroxide. Fractions shown to contain product were combined and concentrated under reduced pressure. The desired product was then isolated by distillation.

Preparation II

N-methyl-N-((S)-1-phenylethyl)-5-amino-2-pentanone

A mixture of 5.85 mL (38.87 mMol) 5-chloro-2-pentanone ethylene glycol ketal, 5.0 gm (37.0 mMol) N-methyl-(S)-1-phenylethylamine, 6.14 gm (37.0 mMol) potassium iodide and 15.33 gm (110.9 mMol) potassium carbonate in 100 mL acetonitrile was stirred at room temperature for 2 days. The reaction mixture was then filtered and the filtrate concentrated under reduced pressure. The residue was dissolved in 50 mL acetone to which was added 50 mL 2N hydrochloric acid. The resulting solution was stirred at room temperature for 3 hours and was then concentrated to half volume under reduced pressure. The residue was extracted diethyl ether (2 ×50 mL) and the remaining aqueous solution was treated with 5N sodium hydroxide until the pH of the solution was about 13. This aqueous phase was now extracted with dichloromethane (3×60 mL). The organic phases were combined, dried over sodium sulfate and concentrated under reduced pressure. The residue was subjected to silica gel chromatography, eluting with 40% ethyl acetated in hexane. Fractions shown to contain product were combined and concentrated under reduced pressure to give 7.11 gm (88%) of the desired compound.

Preparation III

N-(4-fluorobenzoyl)-4-aminophenylhydrazine
Acylation of 4-nitroaniline

To a stirred suspension of 19.83 gm (143.56 mMol) 4-nitroaniline in 150 mL dichloromethane and 12.9 mL (159.5 mMol) pyridine at 0° C. were slowly added 24.5 gm (154.8 mMol) 4-fluorobenzoyl chloride. The reaction mixture was then stirred for 15 minutes at 0° C., at which time the reaction mixture became homogeneous, and then for an hour at room temperature. To this mixture were then added 100 mL water and the solid which formed was collected by filtration. The filter cake was washed with hexane (80 mL) followed by water (100 mL) and it was then dried under vacuum at 60° C. to give 34.1 gm (91%) N-(4-fluorobenzoyl)-4-nitroaniline.

m.p.=117–118° C.

MS(FD): m/e=260 (M$^+$)

Catalytic hydrogenation of nitro group

A mixture of 32.25 gm (124 mMol) N-(4-fluorobenzoyl)-4-nitroaniline and 3.2 gm platinum on carbon in 500 mL tetrahydrofuran was hydrogenated at room temperature for 18 hours with an initial pressure of 60 p.s.i. The reaction mixture was then filtered and the filtrate concentrated under reduced pressure to give 22.45 gm (79%) of N-(4-fluorobenzoyl)-4-aminoaniline.

Diazotization and reduction

To a stirred suspension of 5.0 gm (23.9 mMol) N-(4-fluorobenzoyl)-4-aminoaniline in 42 mL concentrated hydrochloric acid at 0° C. was added dropwise a solution of 1.65 gm (23.9 mMol) sodium nitrite in 30 mL water. The mixture was stirred for 10 minutes after the addition was complete and was then added dropwise to a solution of 19.6 gm (86.87 mMol) stannous chloride dihydrate in 40 mL concentrated hydrochloric acid at 0° C. The resultant white paste was stirred vigorously for 1 hour and was then filtered under vacuum. The solid which formed was then partitioned between ethyl acetate and 5N sodium hydroxide, the phases separated and the aqueous phase was extracted again with dichloromethane. The combined organic phases were combined, dried over sodium sulfate and concentrated under reduced pressure to give 3.8 gm (72%) of the title compound as a brown solid which is suitable for use in subsequent reactions without further purification.

Preparation IV

2-methyl-5-amino-3-(2-[N',N'-dimethylamino]ethyl)-1H-indole

A mixture of 1.58 gm (4.65 mMol) N-[2-methyl-3-(2-[N',N'-dimethylamino]ethyl)-1H-indol-5-yl]-4-fluorobenzamide and 40 mL 6N hydrochloric acid was heated to reflux for 4 hours. The reaction mixture was then cooled to room temperature and then extracted with benzene (3×70 mL). The remaining aqueous phase was treated with 5N sodium hydroxide until pH of about 11–12. The aqueous phase was then extracted with dichloromethane (4×100 mL) and the combined extracts were dried over sodium sulfate and concentrated under reduced pressure. The resultant residue was subjected to silica gel chromatography, eluting with dichloromethane containing 14% methanol and 1% ammonium hydroxide. Fractions shown to contain product were combined and concentrated under reduced pressure to give 0.71 gm (70%) of the title compound.

MS(FAB): m/e=218 (M+1)

Preparation V

N-[2-methyl-3-(2-[N'-methylamino]ethyl)-1H-indol-5-yl]-4-fluorobenzamide

A mixture of 3.74 gm (8.7 mMol) N-[2-methyl-3-(2-[N'-methyl-N'-((S)-1-phenylethyl)amino]ethyl)-1H-indol-5-yl]-4-fluorobenzamide, 5.49 gm (87.1 mMol) ammonium formate and 0.4 gm 5% palladium on carbon in 80 mL methanol was heated at reflux for 45 minutes. The reaction mixture was filtered and the filtrate concentrated under reduced pressure. The resulting residue was subjected to flash chromatography, eluting with dichloromethane containing 20% methanol and 2% ammonium hydroxide. Fractions shown to contain product were combined and concentrated under reduced pressure to give 1.93 gm (68%) of the title compound.

m.p.=82–84° C.

MS: Exact Mass: Calculated for: $C_{19}H_{21}N_3OF$=326.1669. Found: 326.1694.

Preparations VI and VII are typical of procedures for the synthesis of the 2-(pyrazol-4-yl)-1-ethanols required for the preparation of compounds of this invention.

Preparation VI 2-(1-methyl-1H-pyrazol-4-yl)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M$^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126(M$^+$)

$^1$H-NMR(DMSO-d$_6$): δ7.45 (s, 1H); 7.25 (s, 1H); 4.65 (t, 1H); 3.75 (s,3H); 3.55 (m, 2H); 2.55 (t, 2H).

Preparation VII 2-(1-isopropyl-1H-pyrazol-4-yl)-1-ethanol

To a solution of 1.0 gm (9.0 mMol) 2-(4-pyrazolyl)-1-ethanol in 36 mL dimethylformamide were added 2.38 gm (22.5 mMol) sodium carbonate followed by the dropwise addition of a solution of 0.89 mL (9.0 mMol) 2-iodopropane in 8 mL dimethylformamide. The reaction mixture was heated to 100° C. for 18 hours. The reaction mixture was then cooled to ambient and then concentrated under reduced pressure. The residue was partitioned between water and dichloromethane. The organic phase was then washed with water followed by saturated aqueous sodium chloride and was then dried over sodium sulfate. The remaining organics were concentrated under reduced pressure to give 0.36 gm (26.0%) of the title compound as a brown oil.

$^1$H-NMR(DMSO-d$_6$): δ7.50 (s, 1H); 7.25 (s, 1H); 4.60 (t, 1H); 4.40 (m, 1H); 3.50 (m, 2H); 2.55 (t, 2H); 1.35 (d, 6H).

Preparation VIII 1-(3-(1-pyrrolidinyl)propyl)-3-ethylcarbodiimide (PEPC)

N-ethyl-N'-3-(1-pyrrolidinyl)propylurea

To a solution of 27.7 gm (0.39 mole) ethyl isocyanate in 250 mL chloroform were added 50 gm (0.39 mole) 3-(1-pyrrolidinyl)propylamine dropwise with cooling. Once the addition was complete, the cooling bath was removed and the reaction mixture stirred at room temperature for 4 hours. The reaction mixture was then concentrated under reduced pressure to give 74.5 gm (96.4%) of the desired urea as a clear oil.

1-(3-(1-pyrrolidinyl)propyl)-3-ethylcarbodiimide (PEPC)

To a solution of 31.0 gm (0.156 mole) N-ethyl-N'-3-(1-pyrrolidinyl)propylurea in 500 mL dichloromethane were added 62.6 gm (0.62 mole) triethylamine and the solution was cooled to 0° C. To this solution were then added 59.17 gm (0.31 mole) 4-toluenesulfonyl chloride in 400 mL dichloromethane dropwise at such a rate as to maintain the reaction at 0–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 gm (67%) of the desired product as a crude orange oil. A portion of the oil was distilled under vacuum to give a colorless oil distilling at 78–82° C. (0.4 mm Hg).

Preparation IX

Preparation of a polymer supported form of 1-(3-(1-pyrrolidinyl)propyl)-3-ethylcarbodiimide (PEPC)

A suspension of 8.75 gm (48.3 mMol) 1-(3-(1-pyrrolidinyl)propyl)-3-ethylcarbodiimide and 24.17 gm (24.17 mMol) Merrifield's resin (2% cross-linked, 200–400 mesh, chloromethylated styrene/divinylbenzene copolymer, 1 meq. Cl/gm) in dimethylformamide was heated at 100° C. for 2 days. The reaction was cooled and filtered and the resulting resin washed sequentially with 1L dimethylformamide, 1L tetrahydrofuran and 1L diethyl ether. The remaining resin was then dried under vacuum for 18 hours.

Preparation X

N-[2-methyl-3-(2-aminoethyl)-1H-indol-5-yl]-4-fluorobenzamide 5-phthalimidyl-2-pentanone ethylene glycol ketal A mixture of 25 gm (0.15 Mol) 5-chloro-2-pentanone ethylene glycol ketal, 42.2 gm (0.23 Mol) potassium phthalimidate, 150 mL ethanol and 150 mL dimethylformamide was heated at reflux for 3 days. The reaction mixture was cooled to room temperature, diluted with water and extracted with ethyl acetate. The organic extract was washed with water, dried over sodium sulfate and concentrated under reduced pressure to provide 36.8 gm (88%) of the desired ketal.

5-phthalimidyl-2-pentanone

A solution of 26.8 gm (97.2 mMol) 5-phthalimidyl-2-pentanone ethylene glycol ketal in 200 mL acetone and 200 mL 3N hydrochloric acid was stirred at room temperature for 14 hours. The reaction mixture was then adjusted to pH=12 with 50% sodium hydroxide and the acetone removed under reduced pressure. The remaining aqueous phase was extracted with ethyl acetate. This organic phase was washed with water, dried over sodium sulfate, and concentrated under reduced pressure to provide 15.8 gm (70%) of the desired ketone.

N-[2-methyl-3-(2-phthalimidylethyl)-1H-indol-5-yl]-4-fluorobenzamide

To a solution of 5.33 gm (21.7 mMol) 4-(4-fluorobenzoyl)aminophenylhydrazine and 5.03 gm (21.8 mMol) 5-phthalimidyl-2-pentanone in 100 mL ethanol were added 2 mL concentrated hydrochloric acid and the reaction mixture was heated at 80° C. for 14 hours. To the reaction mixture were then added an additional 3 mL concentrated hydrochloric acid and heating continued for an additional 6 hours. The reaction mixture was then cooled to 0° C. and 100 mL hexane were slowly added. The solid which formed was filtered and washed with hexane and provided, after drying, 6.67 gm of the desired compound. The mother liquor was concentrated under reduced pressure and then subjected to silica gel chromatography, eluting with 1:1 hexane:ethyl acetate. Fractions containing product were combined and concentrated under reduced pressure to provide an additional 0.63 gm of product. Overall yield was 7.3 gm (76%).

Removal of phthalimidyl moiety

A mixture of 5.63 gm (12.8 mMol) N-[2-methyl-3-(2-phthalimidylethyl)-1H-indol-5-yl]-4-fluorobenzamide, 13.5 mL hydrazine hydrate, 45 mL water, and 18 mL ethanol was stirred at room temperature for 16 hours. The reaction mixture was concentrated under reduced pressure and the residue partitioned between dichloromethane and saturated aqueous sodium carbonate. The phases were separated and the aqueous phase was extracted twice with dichloromethane containing 5% methanol. All organic phases wee combined, dried over sodium sulfate and concentrated under reduced pressure. The residue was subjected to silica gel chromatography, eluting with 15% methanol in dichloromethane containing 1% ammonium hydroxide. Fractions containing product were combined and concentrated under reduced pressure to provide 3.5 gm (89%) of the title amine as a solid.

m.p.=80–82° C.

MS(m/e): 311(M$^+$)

The Fischer indolization conditions described in detail in Example 1 are typical of those required to prepare the compounds of the present invention.

EXAMPLE 1

N-[2-methyl-3-(2-[N',N'-dimethylamino]ethyl)-1H-indol-5-yl]-4-fluorobenzamide hydrochloride To a solution of 4.00 gm (30.96 mMol) N,N-dimethyl-5-amino-2-pentanone and 7.74 gm (31.6 mMol) N-(4-fluorobenzoyl)-4-aminohydrazine in 140 mL ethanol were added 1.5 mL concentrated hydrochloric acid and the reaction mixture was heated to reflux for 3 hours. At this point an additional 6.0 mL concentrated hydrochloric acid were added and the reflux was continued for 36 hours. The reaction mixture was concentrated to half volume under reduced pressure and was then diluted with 300 mL dichloromethane followed by 200 mL 1N sodium hydroxide. The organic phase was separated and the aqueous phase extracted dichloromethane (4×150 mL). The organic extracts were combined, dried over sodium sulfate and concentrated under reduced pressure. The resulting residue was subjected to flash chromatography, eluting with dichloromethane containing 10% methanol and 1% ammonium hydroxide. Fractions shown to contain product were combined and concentrated under reduced pressure to give 6.66 gm (63.3%) N-[2-methyl-3-(2-[N',N'-dimethylamino]ethyl)-1H-indol-5-yl]-4-fluorobenzamide. This material was converted to the hydrochloride salt, crystallizing from ethanol/diethyl ether to give the title compound.

m.p.=281–283° C.

MS: m/e=339 (M$^+$)

Calculated for $C_{20}H_{22}N_3OF \cdot HCl$: Theory: C, 63.91; H, 6.17; N, 11.18. Found: C, 64.20; H, 6.29; N, 11.20.

EXAMPLE 2

N-[2-methyl-3-(2-[N'-methyl-N'-((S)-1-phenylethyl)amino]ethyl)-1H-indol-5-yl]-4-fluorobenzamide Following the procedure described in detail in Example 1, 5.32 gm (21.7 mMol) N-(4-fluorobenzoyl)-4-aminohydrazine and 2.95 gm (13.45 mMol) N-methyl-N-((S)-1-phenylethyl)-5-amino-2-pentanone were reacted together to prepare 4.988 gm (86%) of the title compound.

m.p.=65–67° C.

MS: m/e=430 (M+1)

Calculated for $C_{27}H_{28}N_3OF$: Theory: C, 75.50; H, 6.57; N, 9.78. Found: C, 75.28; H, 6.75; N, 9.93.

EXAMPLE 3

N-[2-methyl-3-(2-[N'-methyl-N'-ethylamino]ethyl)-1H-indol-5-yl]-4-fluorobenzamide A mixture of 0.125 gm (0.38 mMol) N-[2-methyl-3-(2-(N'-methylamino)ethyl)-1H-indol-5-yl]-4-fluorobenzamide, 0.033 mL (0.41 mMol) ethyl iodide and 0.105 gm (0.76 mMol) potassium carbonate in 4.0 mL acetonitrile was heated at reflux for 6 hours. To the reaction mixture were then added 15.0 mL water and 40 mL dichloromethane. The phases were separated and the aqueous phase was extracted with dichloromethane (2×15 mL). The combined organic phases were dried over sodium sulfate and concentrated under reduced pressure. The resultant residue was subjected to silica gel chromatography, eluting with dichloromethane containing 10% methanol and 1% ammonium hydroxide. Fractions shown to contain product were combined and concentrated under reduced pressure to give 0.040 gm (30%) of the title compound.

m.p.=79–81° C.

MS: m/e=353 (M$^+$)

The compounds of Examples 4–8 were prepared by the procedure described in detail in Example 3.

EXAMPLE 4

N-(2-methyl-3-(2-(N'-methyl-N'-propylamino)ethyl)-1H-indol-5-yl)-4-fluorobenzamide hydrobromide Beginning with 0.152 gm (0.467 mMol) N-[(2-methyl-3-(2-[N'-methylamino]ethyl)-1H-indol-5-yl]-4-fluorobenzamide and 0.068 mL (0.697 mMol) 1-iodopropane, 0.071 gm (41%) of N-[2-methyl-3-(2-[N'-methyl-N-propylamino]ethyl)-1H-indol-5-yl]-4-fluorobenzamide were prepared. The hydrobromide salt was prepared and crystallized from ethanol/diethyl ether to give the title compound.

m.p.=97–99° C.

MS: Exact Mass: Calculated for: $C_{22}H_{27}N_3OF=368.2138$. Found: 368.2135.

EXAMPLE 5

N-[2-methyl-3-(2-[N'-methyl-N'-cyclohexylmethylamino]ethyl)-1H-indol-5-yl]-4-fluorobenzamide hydrobromide Beginning with 0.166 gm (0.51 mMol) N-[2-methyl-3-(2-[N'-methylamino]ethyl-1H-indol-5-yl]-4- fluorobenzamide and 0.085 mL (0.61 mMol) cyclohexylmethyl bromide, 0.170 gm (79%) of N-[2-methyl-3-(2-[N'-methyl-N'-cyclopropylmethylamino]ethyl)-1H-indol-5-yl]-4-fluorobenzamide were prepared. The hydrobromide salt was prepared and crystallized from ethanol/diethyl ether to give the title compound.

m.p.=195–198° C.

MS: m/e=422 (M+1)

Calculated for $C_{26}H_{33}N_3OF \cdot HBr$: Theory: C, 62.05; H, 6.62; N, 8.36. Found: C, 61.96; H, 6.71; N, 8.25.

EXAMPLE 6

N-[2-methyl-3-(2-[N'-methyl-N'-(2-phenylethyl)amino]ethyl)-1H-indol-5-yl]-4-fluorobenzamide hydrochloride Beginning with 0.215 gm (0.66 mMol) N-[(2-methyl-3-(2-[N'-methylamino]ethyl)-1H-indol-5-yl]-4-fluorobenzamide and 0.12 mL (0.88 mMol) 2-phenylethyl bromide, 0.225 gm (80%) of N-[2-methyl-3-(2-[N'-methyl-N'-(2-phenylethyl)amino]ethyl)-1H-indol-5-yl]-4-fluorobenzamide were prepared. The hydrochloride salt was prepared and crystallized from ethanol/diethyl ether to give the title compound.

m.p.=221–223° C.

MS: m/e=429 (M$^+$)

Calculated for $C_{27}H_{28}N_3OF \cdot HCl$: Theory: C, 69.59; H, 6.27; N, 9.02. Found: C, 69.84; H, 6.38; N, 8.87.

EXAMPLE 7

N-[2-methyl-3-(2-[N'-methyl-N'-(4-pyridinylmethyl)amino]ethyl)-1H-indol-5-yl]-4-fluorobenzamide Beginning with 0.139 gm (0.43 mMol) N-[2-methyl-3-(2-[N'-methylamino]ethyl)-1H-indol-5-yl]-4-fluorobenzamide and 0.100 gm (0.61 mMol) 4-pyridinylmethyl chloride hydrochloride, 0.145 gm (82%) of the title compound were prepared.

m.p.=77–80° C.

MS: m/e=416 (M$^+$)

MS: Exact Mass: Calculated for $C_{25}H_{26}N_4OF=417.2091$. Found: 417.2082.

EXAMPLE 8

N-[2-methyl-3-(2-[N'-methyl-N'-(2-[1-methylpyrazol-4-yl]ethyl)amino]ethyl)-1H-indol-5-yl]-4-fluorobenzamide hydrochloride Beginning with 0.209 gm (0.64 mMol) N-[(2-methyl-3-(2-[N'-methylamino]ethyl)-1H-indol-5-yl]-4-fluorobenzamide and 0.195 gm (0.95 mMol) 2-(1-methyl-1H-pyrazol-3-yl)-1-methanesulfonyloxyethane, 0.204 gm (74%) of N-[2-methyl-3-(2-[N'-methyl-N'-(2-[1-methylpyrazol-4-yl]ethyl)amino]ethyl)-1H-indol-5-yl]-4-fluorobenzamide were recovered. This compound was converted to its hydrochloride salt, crystallizing from ethanol/diethyl ether to give the title compound.

m.p.=84–86° C.

MS: m/e=433 (M$^+$)

MS: Exact Mass: Calculated for $C_{25}H_{29}N_5OF=434.2356$. Found: 434.2363.

EXAMPLE 9

N-[2-methyl-3-(2-[N',N'-dimethylamino]ethyl)-1H-indol-5-yl]-4-methylthiobenzamide A mixture of 0.142 gm (0.65 mMol) 2-methyl-5-amino-3-(2-(N',N'-dimethylamino)ethyl)-1H-indole, 0.12 gm (0.71 mMol) 4-methylthiobenzoic acid, 0.096 gm (0.71 mMol) 1-hydroxybenzotriazole, and 0.136 gm (0.71 mMol) 1-(3-dimethylaminopropyl)-3-ethylcarbodiimide hydrochloride (EDC) in 8 mL dimethylformamide and 1 mL tetrahydrofuran was stirred at room temperature under a nitrogen atmosphere for 48 hours. The the mixture were then added 50 mL dichloromethane, 5 mL 2N sodium hydroxide and 50 mL water. The phases were separated and the aqueous layer extracted with dichloromethane (3×30 mL). The combined organic layers were dried over sodium sulfate and concentrated under reduced pressure. The resulting residue was subjected to silica gel chromatography, eluting with dichloromethane containing 10% methanol and 1% ammonium hydroxide. Fractions shown to contain product were combined and concentrated under reduced pressure to give 0.134 gm (56%) of the title compound.

m.p.=87–91° C.

MS: Exact Mass: Calculated for $C_{21}H_{26}N_3OS=368.1797$. Found: 368.1808.

The compounds of Examples 10–14 were prepared by the procedure described in detail in Example 9.

EXAMPLE 10

N-[2-methyl-3-(2-[N',N'-dimethylamino]ethyl)-1H-indol-5-yl]-4-(N'',N''-dimethylamino)benzamide Beginning with 0.148 gm (0.68 mMol) 2-methyl-5-amino-3-(2-(N',N'-dimethylamino)ethyl)-1H-indole and 0.113 gm (0.68 mMol) 4-(dimethylamino)benzoic acid, 0.080 gm (32%) of the title compound were recovered.

m.p.=100–104° C. (decomp.)

Calculated for $C_{22}H_{28}N_4O$: Theory: C, 72.50; H, 7.74; N, 15.37. Found: C, 72.26; H, 7.56; N, 15.33.

EXAMPLE 11

N-[2-methyl-3-(2-[N',N'-dimethylamino]ethyl)-1H-indol-5-yl]-4-acetamidobenzamide Beginning with 0.130 gm (0.598 mMol) 2-methyl-5-amino-3-(2-(N',N'-dimethylamino)ethyl)-1H-indole and 0.107 gm (0.598 mMol) 4-acetamidobenzoic acid, 0.130 gm (32%) of the title compound were recovered.

m.p.=134–138° C.

MS: Exact Mass: Calculated for $C_{22}H_{26}N_4O_2=379.2134$. Found: 379.2142.

EXAMPLE 12

N-[2-methyl-3-(2-[N',N'-dimethylamino]ethyl)-1H-indol-5-yl]-4-(2-methyl-4-fluoro)benzamide Beginning with 0.148 gm (0.68 mMol) 2-methyl-5-amino-3-(2-(N',N'-dimethylamino)ethyl)-1H-indole and 0.115 gm (0.75 mMol) 2-methyl-4-fluorobenzoic acid, 0.206 gm (86%) of the title compound were recovered.

m.p.=71–75° C.

MS: Exact Mass: Calculated for $C_{21}H_{25}N_3OF=354.1982$. Found: 354.1993.

EXAMPLE 13

N-[2-methyl-3-(2-[N',N'-dimethylamino]ethyl)-1H-indol-5-yl]-2-acetamido-4-fluorobenzamide Beginning with 0.150 gm (0.69 mMol) 2-methyl-5-amino-3-(2-(N',N'-dimethylamino)ethyl)-1H-indole and 0.150 gm (0.76 mMol) 2-acetamido-4-fluorobenzoic acid, 0.150 gm (55%) of the title compound were recovered.

m.p.=183–187° C.

MS(FD): m/e=396 (M$^+$)

EXAMPLE 14

N-[2-methyl-3-(2-[N',N'-dimethylamino]ethyl)-1H-indol-5-yl]-6-fluoropyridin-3-ylcarboxamide Beginning with 0.141 gm (0.65 mMol) 2-methyl-5-amino-3-(2-(N',N'-dimethylamino)ethyl)-1H-indole and 0.101 gm (0.71 mMol) 6-fluoro-3-pyridinecarboxylic acid, 0.0935 gm (42%) of the title compound were recovered.

m.p.=165–168° C.

MS: Exact Mass: Calculated for $C_{19}H_{22}N_4OF$=341.1778. Found: 341.1783.

EXAMPLE 15

N-[2-methyl-3-(2-[N',N'-dimethylamino]ethyl)-1H-indol-5-yl]-2-chloro-4-fluorobenzamide hydrobromide To a stirred solution of 0.115 gm (0.66 mMol) 2-chloro-4-fluorobenzoic acid in 2 mL dimethylformamide were added 0.107 gm (0.66 mMol) carbonyldiimidazole (CDI) and immediate gas evolution was observed. The reaction mixture was stirred for 5 hours at room temperature and then 0.131 gm (0.60 mMol) 2-methyl-5-amino-3-(2-(N',N'-dimethylamino)ethyl)-1H-indole were added. The resulting mixture was stirred at room temperature for 72 hours. The reaction mixture was then concentrated under reduced pressure and the residue subjected to silica gel chromatography. The material isolated was further purified by silica gel chromatography, eluting with dichloromethane containing 7% methanol and 1% ammonium hydroxide. Fractions shown to contain product were combined and concentrated under reduced pressure to give 0.107 gm (43%) of N-[2-methyl-3-(2-[N',N'-dimethylamino]ethyl)-1H-indol-5-yl]-2-chloro-4-fluorobenzamide. The hydrobromide salt was formed and crystallized from ethanol/diethyl ether to give the title compound.

m.p.=66–68° C.

MS: m/e=373 (M$^+$)

EXAMPLE 16

N-[2-methyl-3-(2-[N',N'-dimethylamino]ethyl)-1H-indol-5-yl]-2,4-difluorobenzamide hydrochloride To a stirred solution of 0.135 gm (0.62 mMol) 2-methyl-5-amino-3-(2-(N',N'-dimethylamino)ethyl)-1H-indole in 6 mL dichloromethane and 0.2 mL pyridine at 0° C. were added 0.09 mL (0.73 mMol) 2,4-difluorobenzoyl chloride. The reaction mixture was warmed to room temperature and stirred for 2 hours at room temperature. The reaction mixture was then diluted with 20 mL dichloromethane and washed with 4 mL 2N sodium hydroxide. The organic phase was separated and the aqueous phase extracted again with dichloromethane. The organic phases were combined, dried over sodium sulfate and concentrated under reduced pressure. The residue was subjected to silica gel chromatography, eluting with dichloromethane containing 8% methanol and 1% ammonium hydroxide. Fractions shown to contain product were combined and concentrated under reduced pressure to give 0.110 gm (50%) of N-[2-methyl-3-(2-[N',N'-dimethylamino]ethyl)-1H-indol- 5-yl]-2,4-difluorobenzamide. The hydrochloride salt was formed and crystallizing from ethanol/diethyl ether to give the title compound.

m.p.=269–271° C.

MS: m/e=357 (M$^+$)

Calculated for $C_{20}H_{21}N_3OF_2$: Theory: C, 60.99; H, 5.63; N, 10.67. Found: C, 61.24; H, 5.74; N, 10.67.

General procedure for the coupling of carboxylic acids with 5-amino-3-(2-(N',N'-dimethylamino)ethyl)-1H-indole To a suspension of 0.120 gm (0.11 mMol) of polymer bound 1-ethyl-3-(3-(1-pyrrolidinylpropyl)carbodiimide (Preparation IX) in 2 mL chloroform are added 6 mg (0.027 mMol) of 5-amino-3-(2-(N',N'-dimethylamino)ethyl)-1H-indole and 0.055 mMol of the desired carboxylic acid. The reaction is agitated for 48 hours at room temperature. The resin is removed by filtration and the product isolated by evaporation of solvent. This procedure is illustrated by Examples 17–34.

EXAMPLE 17

N-[2-methyl-3-(2-[N',N'-dimethylamino]ethyl)-1H-indol-5-yl]isobutyramide

Beginning with 0.027 mMol of 2-methyl-5-amino-3-(2-(N',N'-dimethylamino)ethyl)-1H-indole and 0.055 mMol of isobutyric acid, the title compound was prepared in 60% yield.

MS: m/e=390 (M$^+$)

EXAMPLE 18

N-[2-methyl-3-(2-[N',N'-dimethylamino]ethyl)-1H-indol-5-yl]cyclopropanecarboxylic amide Beginning with 0.027 mMol of 2-methyl-5-amino-3-(2-(N',N'-dimethylamino)ethyl)-1H-indole and 0.055 mMol of cyclopropanecarboxylic acid, the title compound was prepared in 65% yield.

EXAMPLE 19

N-[2-methyl-3-(2-[N',N'-dimethylamino]ethyl)-1H-indol-5-yl]-3-trifluoromethylbenzamide Beginning with 0.027 mMol of 2-methyl-5-amino-3-(2-(N',N'-dimethylamino)ethyl)-1H-indole and 0.055 mMol of 3-trifluoromethylbenzoic acid, the title compound was prepared in 55% yield.

MS: m/e=390 (M$^+$)

EXAMPLE 20

N-[2-methyl-3-(2-[N',N'-dimethylamino]ethyl)-1H-indol-5-yl]-3,5-dichlorobenzamide Beginning with 0.027 mMol of 2-methyl-5-amino-3-(2-(N',N'-dimethylamino)ethyl)-1H-indole and 0.055 mMol of 3,5-dichlorobenzoic acid, the title compound was prepared in 55% yield.

EXAMPLE 21

N-[2-methyl-3-(2-[N',N'-dimethylamino]ethyl)-1H-indol-5-yl]-2-methoxy-4-chlorobenzamide Beginning with 0.027 mMol of 2-methyl-5-amino-3-(2-(N',N'-dimethylamino)ethyl)-1H-indole and 0.055 mMol of 2-methoxy-4-chlorobenzoic acid, the title compound was prepared in 33% yield.

MS: m/e=386 (M$^+$)

EXAMPLE 22

N-[2-methyl-3-(2-[N',N'-dimethylamino]ethyl)-1H-indol-5-yl]-2-chloro-4-nitrobenzamide Beginning with 0.027 mMol of 2-methyl-5-amino-3-(2-(N',N'-dimethylamino)ethyl)-1H-indole and 0.055 mMol of 2-chloro-4-nitrobenzoic acid, the title compound was prepared in 27% yield.

MS: m/e=401 (M+)

EXAMPLE 23

N-[2-methyl-3-(2-[N',N'-dimethylamino]ethyl)-1H-indol-5-yl]-2-furylcarboxamide

Beginning with 0.027 mMol of 2-methyl-5-amino-3-(2-(N',N'-dimethylamino)ethyl)-1H-indole and 0.055 mMol of 2-furylcarboxylic acid, the title compound was prepared in 67% yield.

EXAMPLE 24

N-[2-methyl-3-(2-[N',N'-dimethylamino]ethyl)-1H-indol-5-yl]-3-furylcarboxamide

Beginning with 0.027 mMol of 2-methyl-5-amino-3-(2-(N',N'-dimethylamino)ethyl)-1H-indole and 0.055 mMol of 3-furylcarboxylic acid, the title compound was prepared in 65% yield.

EXAMPLE 25

N-[2-methyl-3-(2-[N',N'-dimethylamino]ethyl)-1H-indol-5-yl]-5-methyl-2-furylcarboxamide Beginning with 0.027 mMol of 2-methyl-5-amino-3-(2-(N',N'-dimethylamino)ethyl)-1H-indole and 0.055 mMol of 5-methyl-2-furylcarboxylic acid, the title compound was prepared in 66% yield.

MS: m/e=326 (M+)

EXAMPLE 26

N-[2-methyl-3-(2-[N',N'-dimethylamino]ethyl)-1H-indol-5-yl]-2-methyl-3-furylcarboxamide Beginning with 0.027 mMol of 2-methyl-5-amino-3-(2-(N',N'-dimethylamino)ethyl)-1H-indole and 0.055 mMol of 2-methyl-3-furylcarboxylic acid, the title compound was prepared in 32% yield.

MS: m/e=326 (M+)

EXAMPLE 27

N-[2-methyl-3-(2-[N',N'-dimethylamino]ethyl)-1H-indol-5-yl]-5-methyl-3-furylcarboxamide Beginning with 0.027 mMol of 2-methyl-5-amino-3-(2-(N',N'-dimethylamino)ethyl)-1H-indole and 0.055 mMol of 5-methyl-3-furylcarboxylic acid, the title compound was prepared in 32% yield.

MS: m/e=326 (M+)

EXAMPLE 28

N-[2-methyl-3-(2-[N',N'-dimethylamino]ethyl)-1H-indol-5-yl]-5-chloro-2-furylcarboxamide Beginning with 0.027 mMol of 2-methyl-5-amino-3-(2-(N',N'-dimethylamino)ethyl)-1H-indole and 0.055 mMol of 5-chloro-2-furylcarboxylic acid, the title compound was prepared in 42% yield.

MS: m/e=346 (M+)

EXAMPLE 29

N-[2-methyl-3-(2-[N',N'-dimethylamino]ethyl)-1H-indol-5-yl]-3-thienylcarboxamide Beginning with 0.027 mMol of 2-methyl-5-amino-3-(2-(N',N'-dimethylamino)ethyl)-1H-indole and 0.055 mMol of 3-thienylcarboxylic acid, the title compound was prepared in 32% yield.

MS: m/e=328 (M+)

EXAMPLE 30

N-[2-methyl-3-(2-[N',N'-dimethylamino]ethyl)-1H-indol-5-yl]-3-methyl-2-thienylcarboxamide Beginning with 0.027 mMol of 2-methyl-5-amino-3-(2-(N',N'-dimethylamino)ethyl)-1H-indole and 0.055 mMol of 3-methyl-2-thienylcarboxylic acid, the title compound was prepared in 50% yield.

MS: m/e=342 (M+)

EXAMPLE 31

N-[2-methyl-3-(2-[N',N'-dimethylamino]ethyl)-1H-indol-5-yl]-5-methyl-2-thienylcarboxamide Beginning with 0.027 mMol of 2-methyl-5-amino-3-(2-(N',N'-dimethylamino)ethyl)-1H-indole and 0.055 mMol of 5-methyl-2-thienylcarboxylic acid, the title compound was prepared in 33% yield.

EXAMPLE 32

N-[2-methyl-3-(2-[N',N'-dimethylamino]ethyl)-1H-indol-5-yl]-5-bromo-2-thienylcarboxamide Beginning with 0.027 mMol of 2-methyl-5-amino-3-(2-(N',N'-dimethylamino)ethyl)-1H-indole and 0.055 mMol of 5-bromo-2-thienylcarboxylic acid, the title compound was prepared in 35% yield.

EXAMPLE 33

N-[2-methyl-3-(2-[N',N'-dimethylamino]ethyl)-1H-indol-5-yl]-5-chloro-2-thienylcarboxamide Beginning with 0.027 mMol of 2-methyl-5-amino-3-(2-(N',N'-dimethylamino)ethyl)-1H-indole and 0.055 mMol of 5-chloro-2-thienylcarboxylic acid, the title compound was prepared in 25% yield.

MS: m/e=362 (M+)

EXAMPLE 34

N-[2-methyl-3-(2-[N',N'-dimethylamino]ethyl)-1H-indol-5-yl]-3-pyridinecarboxamide Beginning with 0.027 mMol of 2-methyl-5-amino-3-(2-(N',N'-dimethylamino)ethyl)-1H-indole and 0.055 mMol of 3-pyridine-carboxylic acid, the title compound was prepared in 33% yield.

MS: m/e=323 (M+)

General procedure for the coupling of carboxylic acid halides with 5-amino-3-(2-(N',N'-dimethylamino)ethyl)-1H-indole To a suspension of 0.041 gm (0.056 mMol) of polymer bound 4-(N,N-dimethylamino)pyridine in 2 mL chloroform are added 6 mg (0.027 mMol) of 2-methyl-5-amino-3-(2-(N',N'-dimethyl-amino)ethyl)-1H-indole and 0.035 mMol of the desired carboxylic acid halide. The reaction is agitated for 24 hours at room temperature. To the reaction mixture are then added 0.07 gm (0.056 mMol) aminomethylated polystyrene and the reaction agitated for an additional 24 hours. The resin is removed by filtration and the product isolated by evaporation of solvent. This procedure is illustrated by Examples 35–83.

EXAMPLE 35

N-[2-methyl-3-(2-[N',N'-dimethylamino]ethyl)-1H-indol-5-yl]acetamide

Beginning with 0.027 mMol of 2-methyl-5-amino-3-(2-(N',N'-dimethylamino)ethyl)-1H-indole and 0.035 mMol of acetyl chloride, the title compound was prepared in 50% yield.

MS: m/e=260 (M⁺)

EXAMPLE 36

N-[2-methyl-3-(2-[N',N'-dimethylamino]ethyl)-1H-indol-5-yl]propanamide

Beginning with 0.027 mMol of 2-methyl-5-amino-3-(2-(N',N'-dimethylamino)ethyl)-1H-indole and 0.035 mMol of propanoyl chloride, the title compound was prepared in 73% yield.

MS: m/e=274 (M⁺)

EXAMPLE 37

N-[2-methyl-3-(2-[N',N'-dimethylamino]ethyl)-1H-indol-5-yl]isobutyramide

Beginning with 0.027 mMol of 2-methyl-5-amino-3-(2-(N',N'-dimethylamino)ethyl)-1H-indole and 0.035 mMol of isobutyryl chloride, the title compound was prepared in 67% yield.

MS: m/e=288 (M⁺)

EXAMPLE 38

N-[2-methyl-3-(2-[N',N'-dimethylamino]ethyl)-1H-indol-5-yl]-4-methylpentanamide

Beginning with 0.027 mMol of 2-methyl-5-amino-3-(2-(N',N'-dimethylamino)ethyl)-1H-indole and 0.035 mMol of 4-methyl-pentanoyl chloride, the title compound was prepared in 70% yield.

MS: m/e=316 (M⁺)

EXAMPLE 39

N-[2-methyl-3-(2-[N',N'-dimethylamino]ethyl)-1H-indol-5-yl]cyclobutanecarboxamide Beginning with 0.027 mMol of 2-methyl-5-amino-3-(2-(N',N'-dimethylamino)ethyl)-1H-indole and 0.035 mMol of cyclobutane-carbonyl chloride, the title compound was prepared in 69% yield.

MS: m/e=300 (M⁺)

EXAMPLE 40

N-[2-methyl-3-(2-[N',N'-dimethylamino]ethyl)-1H-indol-5-yl]cyclopentanecarboxamide Beginning with 0.027 mMol of 2-methyl-5-amino-3-(2-(N',N'-dimethylamino)ethyl)-1H-indole and 0.035 mMol of cyclo-pentanecarbonyl chloride, the title compound was prepared in 63% yield.

MS: m/e=314 (M⁺)

EXAMPLE 41

N-[2-methyl-3-(2-[N',N'-dimethylamino]ethyl)-1H-indol-5-yl]cyclohexanecarboxamide Beginning with 0.027 mMol of 2-methyl-5-amino-3-(2-(N',N'-dimethylamino)ethyl)-1H-indole and 0.035 mMol of cyclohexane-carbonyl chloride, the title compound was prepared in 80% yield.

MS: m/e=328 (M⁺)

EXAMPLE 42

N-[2-methyl-3-(2-[N',N'-dimethylamino]ethyl)-1H-indol-5-yl]benzamide

Beginning with 0.027 mMol of 2-methyl-5-amino-3-(2-(N',N'-dimethylamino)ethyl)-1H-indole and 0.035 mMol of benzoyl chloride, the title compound was prepared in 83% yield.

MS: m/e=321 (M⁺)

EXAMPLE 43

N-[2-methyl-3-(2-[N',N'-dimethylamino]ethyl)-1H-indol-5-yl]-4-fluorobenzamide

Beginning with 0.027 mMol of 2-methyl-5-amino-3-(2-(N',N'-dimethylamino)ethyl)-1H-indole and 0.035 mMol of 4-fluorobenzoyl chloride, the title compound was prepared in 73% yield.

MS: m/e=339 (M⁺)

EXAMPLE 44

N-[2-methyl-3-(2-[N',N'-dimethylamino]ethyl)-1H-indol-5-yl]-3-fluorobenzamide

Beginning with 0.027 mMol of 2-methyl-5-amino-3-(2-(N',N'-dimethylamino)ethyl)-1H-indole and 0.035 mMol of 3-fluorobenzoyl chloride, the title compound was prepared in 63% yield.

MS: m/e=340 (M+1)

EXAMPLE 45

N-[2-methyl-3-(2-[N',N'-dimethylamino]ethyl)-1H-indol-5-yl]-2-fluorobenzamide

Beginning with 0.027 mMol of 2-methyl-5-amino-3-(2-(N',N'-dimethylamino)ethyl)-1H-indole and 0.035 mMol of 2-fluorobenzoyl chloride, the title compound was prepared in 76% yield.

MS: m/e=340 (M+1)

EXAMPLE 46

N-[2-methyl-3-(2-[N',N'-dimethylamino]ethyl)-1H-indol-5-yl]-3-chlorobenzamide

Beginning with 0.027 mMol of 2-methyl-5-amino-3-(2-(N',N'-dimethylamino)ethyl)-1H-indole and 0.035 mMol of 3-chlorobenzoyl chloride, the title compound was prepared in 62% yield.

MS: m/e=356 (M⁺)

EXAMPLE 47

N-[2-methyl-3-(2-[N',N'-dimethylamino]ethyl)-1H-indol-5-yl]-4-chlorobenzamide

Beginning with 0.027 mMol of 2-methyl-5-amino-3-(2-(N',N'-dimethylamino)ethyl)-1H-indole and 0.035 mMol of 4-chlorobenzoyl chloride, the title compound was prepared in 66% yield.

EXAMPLE 48

N-[2-methyl-3-(2-[N',N'-dimethylamino]ethyl)-1H-indol-5-yl]-4-methylbenzamide

Beginning with 0.027 mMol of 2-methyl-5-amino-3-(2-(N',N'-dimethylamino)ethyl)-1H-indole and 0.035 mMol of 4-methylbenzoyl chloride, the title compound was prepared in 84% yield.

MS: m/e=336 (M⁺)

EXAMPLE 49

N-[2-methyl-3-(2-[N',N'-dimethylamino]ethyl)-1H-indol-5-yl]-2-methylbenzamide

Beginning with 0.027 mMol of 2-methyl-5-amino-3-(2-(N',N'-dimethylamino)ethyl)-1H-indole and 0.035 mMol of 2-methylbenzoyl chloride, the title compound was prepared in 95% yield.

MS: m/e=336 (M+)

EXAMPLE 50

N-[2-methyl-3-(2-[N',N'-dimethylamino]ethyl)-1H-indol-5-yl]-4-trifluoromethylbenzamide Beginning with 0.027 mMol of 2-methyl-5-amino-3-(2-(N',N'-dimethylamino)ethyl)-1H-indole and 0.035 mMol of 4-trifluoromethylbenzoyl chloride, the title compound was prepared in 87% yield.

MS: m/e=390 (M+)

EXAMPLE 51

N-[2-methyl-3-(2-[N',N'-dimethylamino]ethyl)-1H-indol-5-yl]-2-trifluoromethylbenzamide Beginning with 0.027 mMol of 2-methyl-5-amino-3-(2-(N',N'-dimethylamino)ethyl)-1H-indole and 0.035 mMol of 2-trifluoromethylbenzoyl chloride, the title compound was prepared in 89% yield.

MS: m/e=390 (M+)

EXAMPLE 52

N-[2-methyl-3-(2-[N',N'-dimethylamino]ethyl)-1H-indol-5-yl]-4-methoxycarbonylbenzamide Beginning with 0.027 mMol of 2-methyl-5-amino-3-(2-(N',N'-dimethylamino)ethyl)-1H-indole and 0.035 mMol of 4-methoxycarbonylbenzoyl chloride, the title compound was prepared in 78% yield.

MS: m/e=380 (M+)

EXAMPLE 53

N-[2-methyl-3-(2-[N',N'-dimethylamino]ethyl)-1H-indol-5-yl]-4-methoxybenzamide

Beginning with 0.027 mMol of 2-methyl-5-amino-3-(2-(N',N'-dimethylamino)ethyl)-1H-indole and 0.035 mMol of 4-methoxybenzoyl chloride, the title compound was prepared in 64% yield.

MS: m/e=351 (M+)

EXAMPLE 54

N-[2-methyl-3-(2-[N',N'-dimethylamino]ethyl)-1H-indol-5-yl]-4-phenylbenzamide

Beginning with 0.027 mMol of 2-methyl-5-amino-3-(2-(N',N'-dimethylamino)ethyl)-1H-indole and 0.035 mMol of 4-phenylbenzoyl chloride, the title compound was prepared in 91% yield.

MS: m/e=398 (M+)

EXAMPLE 55

N-[2-methyl-3-(2-[N',N'-dimethylamino]ethyl)-1H-indol-5-yl]-2,3-difluorobenzamide Beginning with 0.027 mMol of 2-methyl-5-amino-3-(2-(N',N'-dimethylamino)ethyl)-1H-indole and 0.035 mMol of 2,3-difluorobenzoyl chloride, the title compound was prepared in 76% yield.

MS: m/e=358 (M+)

EXAMPLE 56

N-[2-methyl-3-(2-[N',N'-dimethylamino]ethyl)-1H-indol-5-yl]-2,6-difluorobenzamide Beginning with 0.027 mMol of 2-methyl-5-amino-3-(2-(N',N'-dimethylamino)ethyl)-1H-indole and 0.035 mMol of 2,6-difluorobenzoyl chloride, the title compound was prepared in 65% yield.

EXAMPLE 57

N-[2-methyl-3-(2-[N',N'-dimethylamino]ethyl)-1H-indol-5-yl]-3,5-difluorobenzamide Beginning with 0.027 mMol of 2-methyl-5-amino-3-(2-(N',N'-dimethylamino)ethyl)-1H-indole and 0.035 mMol of 3,5-difluorobenzoyl chloride, the title compound was prepared in 85% yield.

EXAMPLE 58

N-[2-methyl-3-(2-[N',N'-dimethylamino]ethyl)-1H-indol-5-yl]-3,4-difluorobenzamide Beginning with 0.027 mMol of 2-methyl-5-amino-3-(2-(N',N'-dimethylamino)ethyl)-1H-indole and 0.035 mMol of 3,4-difluorobenzoyl chloride, the title compound was prepared in 75% yield.

EXAMPLE 59

N-[2-methyl-3-(2-[N',N'-dimethylamino]ethyl)-1H-indol-5-yl]-2,5-difluorobenzamide Beginning with 0.027 mMol of 2-methyl-5-amino-3-(2-(N',N'-dimethylamino)ethyl)-1H-indole and 0.035 mMol of 2,5-difluorobenzoyl chloride, the title compound was prepared in 86% yield.

MS: m/e=358 (M+)

EXAMPLE 60

N-[2-methyl-3-(2-[N',N'-dimethylamino]ethyl)-1H-indol-5-yl]-3,4-dichlorobenzamide Beginning with 0.027 mMol of 2-methyl-5-amino-3-(2-(N',N'-dimethylamino)ethyl)-1H-indole and 0.035 mMol of 3,4-dichlorobenzoyl chloride, the title compound was prepared in 69% yield.

EXAMPLE 61

N-[2-methyl-3-(2-[N',N'-dimethylamino]ethyl)-1H-indol-5-yl]-2,6-dichlorobenzamide Beginning with 0.027 mMol of 2-methyl-5-amino-3-(2-(N',N'-dimethylamino)ethyl)-1H-indole and 0.035 mMol of 2,6-dichlorobenzoyl chloride, the title compound was prepared in 69% yield.

EXAMPLE 62

N-[2-methyl-3-(2-[N',N'-dimethylamino]ethyl)-1H-indol-5-yl]-2,4-dichlorobenzamide Beginning with 0.027 mMol of 2-methyl-5-amino-3-(2-(N',N'-dimethylamino)ethyl)-1H-indole and 0.035 mMol of 2,4-dichlorobenzoyl chloride, the title compound was prepared in 64% yield.

MS: m/e=392 (M+1)

EXAMPLE 63

N-[2-methyl-3-(2-[N',N'-dimethylamino]ethyl)-1H-indol-5-yl]-2,3-dichlorobenzamide Beginning with 0.027 mMol of 2-methyl-5-amino-3-(2-(N',N'-dimethylamino)ethyl)-1H indole and 0.035 mMol of 2,3-dichlorobenzoyl chloride, the title compound was prepared in 61% yield.

MS: m/e=392 (M−1)

EXAMPLE 64

N-[2-methyl-3-(2-[N',N'-dimethylamino]ethyl)-1H-indol-5-yl]-2,3,6-trifluorobenzamide Beginning with 0.027 mMol of 2-methyl-5-amino-3-(2-(N',N'-dimethylamino)ethyl)-1H-indole and 0.035 mMol of 2,3,6-trifluorobenzoyl chloride, the title compound was prepared in 86% yield.

MS: m/e=376 (M$^+$)

EXAMPLE 65

N-[2-methyl-3-(2-[N',N'-dimethylamino]ethyl)-1H-indol-5-yl]-2,3,4-trifluorobenzamide Beginning with 0.027 mMol of 2-methyl-5-amino-3-(2-(N',N'-dimethylamino)ethyl)-1H-indole and 0.035 mMol of 2,3,4-trifluorobenzoyl chloride, the title compound was prepared in 70% yield.

EXAMPLE 66

N-[2-methyl-3-(2-[N',N'-dimethylamino]ethyl)-1H-indol-5-yl]-2,4,5-trifluorobenzamide Beginning with 0.027 mMol of 2-methyl-5-amino-3-(2-(N',N'-dimethylamino)ethyl)-1H-indole and 0.035 mMol of 2,4,5-trifluorobenzoyl chloride, the title compound was prepared in 81% yield.

EXAMPLE 67

N-[2-methyl-3-(2-[N',N'-dimethylamino]ethyl)-1H-indol-5-yl]-2,4,6-trifluorobenzamide Beginning with 0.027 mMol of 2-methyl-5-amino-3-(2-(N',N'-dimethylamino)ethyl)-1H-indole and 0.035 mMol of 2,4,6-trifluorobenzoyl chloride, the title compound was prepared in 76% yield.

EXAMPLE 68

N-[2-methyl-3-(2-[N',N'-dimethylamino]ethyl)-1H-indol-5-yl]-2,4,6-trichlorobenzamide Beginning with 0.027 mMol of 2-methyl-5-amino-3-(2-(N',N'-dimethylamino)ethyl)-1H-indole and 0.035 mMol of 2,4,6-trichlorobenzoyl chloride, the title compound was prepared in 59% yield.

EXAMPLE 69

N-[2-methyl-3-(2-[N',N'-dimethylamino]ethyl)-1H-indol-5-yl]-2-trifluoromethyl-4-fluorobenzamide Beginning with 0.027 mMol of 2-methyl-5-amino-3-(2-(N',N'-dimethylamino)ethyl)-1H-indole and 0.035 mMol of 2-trifluoromethyl-4-fluorobenzoyl chloride, the title compound was prepared in 49% yield.

EXAMPLE 70

N-[2-methyl-3-(2-[N',N'-dimethylamino]ethyl)-1H-indol-5-yl]-4-trifluoromethyl-2-fluorobenzamide Beginning with 0.027 mMol of 2-methyl-5-amino-3-(2-(N',N'-dimethylamino)ethyl)-1H-indole and 0.035 mMol of 4-trifluoromethyl-2-fluorobenzoyl chloride, the title compound was prepared in 71% yield.

EXAMPLE 71

N-[2-methyl-3-(2-[N',N'-dimethylamino]ethyl)-1H-indol-5-yl]-2-trifluoromethyl-6-fluorobenzamide Beginning with 0.027 mMol of 2-methyl-5-amino-3-(2-(N',N'-dimethylamino)ethyl)-1H-indole and 0.035 mMol of 2-trifluoromethyl-6-fluorobenzoyl chloride, the title compound was prepared in 66% yield.

EXAMPLE 72

N-[2-methyl-3-(2-[N',N'-dimethylamino]ethyl)-1H-indol-5-yl]-3-trifluoromethyl-4-fluorobenzamide Beginning with 0.027 mMol of 2-methyl-5-amino-3-(2-(N',N'-dimethylamino)ethyl)-1H-indole and 0.035 mMol of 3-trifluoromethyl-4-fluorobenzoyl chloride, the title compound was prepared in 75% yield.

EXAMPLE 73

N-[2-methyl-3-(2-[N',N'-dimethylamino]ethyl)-1H-indol-5-yl]-2,4-dichloro-5-fluorobenzamide Beginning with 0.027 mMol of 2-methyl-5-amino-3-(2-(N',N'-dimethylamino)ethyl)-1H-indole and 0.035 mMol of 2,4-dichloro-5-fluorobenzoyl chloride, the title compound was prepared in 75% yield.

EXAMPLE 74

N-[2-methyl-3-(2-[N',N'-dimethylamino]ethyl)-1H-indol-5-yl]thiophene-2-carboxamide Beginning with 0.027 mMol of 2-methyl-5-amino-3-(2-(N',N'-dimethylamino)ethyl)-1H-indole and 0.035 mMol of thiophene-2-carbonyl chloride, the title compound was prepared in 63% yield.

MS: m/e=328 (M$^+$)

EXAMPLE 75

N-[2-methyl-3-(2-[N',N'-dimethylamino]ethyl)-1H-indol-5-yl]isoxazole-5-carboxamide Beginning with 0.027 mMol of 2-methyl-5-amino-3-(2-(N',N'-dimethylamino)ethyl)-1H-indole and 0.035 mMol of isoxazole-5-carbonyl chloride, the title compound was prepared in 63% yield.

EXAMPLE 76

N-[2-methyl-3-(2-[N',N'-dimethylamino]ethyl)-1H-indol-5-yl]-2-chloropyridine-3-carboxamide Beginning with 0.027 mMol of 2-methyl-5-amino-3-(2-(N',N'-dimethylamino)ethyl)-1H-indole and 0.035 mMol of 2-chloropyridine-3-carbonyl chloride, the title compound was prepared in 60% yield.

EXAMPLE 77

N-[2-methyl-3-(2-[N',N'-dimethylamino]ethyl)-1H-indol-5-yl]-6-chloropyridine-3-carboxamide Beginning with O.027 mMol of 2methyl-5-amino-3-(2-(N',N'-dimethylamino)ethyl)-1H-indole and 0.035 mMol of 6-chloropyridine-3-carbonyl chloride, the title compound was prepared in 68% yield.

EXAMPLE 78

N-[2-methyl-3-(2-[N',N'-dimethylamino]ethyl)-1H-indol-5-yl]-3-chlorothiophene-2-carboxamide Beginning with 0.027 mMol of 2-methyl-5-amino-3-(2-(N',N'-dimethylamino)ethyl)-1H-indole and 0.035 mMol of 3-chlorothiophene-2-carbonyl chloride, the title compound was prepared in 77% yield.

MS: m/e=362 (M$^+$)

EXAMPLE 79

N-[2-methyl-3-(2-[N',N'-dimethylamino]ethyl)-1H-indol-5-yl]naphthalene-2-carboxamide Beginning with 0.027 mMol of 2-methyl-5-amino-3-(2-(N',N'-dimethylamino)ethyl)-1H-indole and 0.035 mMol of naphthalene-2-carbonyl chloride, the title compound was prepared in 67% yield.

MS: m/e=372 (M$^+$)

EXAMPLE 80

N-[2-methyl-3-(2-[N',N'-dimethylamino]ethyl)-1H-indol-5-yl]naphthalene-1-carboxamide Beginning with 0.027 mMol of 2-methyl-5-amino-3-(2-(N',N'-dimethylamino)ethyl)-1H-indole and 0.035 mMol of naphthalene-1-carbonyl chloride, the title compound was prepared in 77% yield.

MS: m/e 372 (M$^+$)

EXAMPLE 81

N-[2-methyl-3-(2-[N',N'-dimethylamino]ethyl)-1H-indol-5-yl]benzothiophene-2-carboxamide Beginning with 0.027 mMol of 2-methyl-5-amino-3-(2-(N',N'-dimethylamino)ethyl)-1H-indole and 0.035 mMol of benzothiophene-2-carbonyl chloride, the title compound was prepared in 53% yield.

MS: m/e=378 (M$^+$)

EXAMPLE 82

N-[2-methyl-3(2 -[N',N'-dimethylamino]ethyl)-1H-indol-5-yl]quinoxaline-2-carboxamide Beginning with 0.027 mMol of 2-methyl-5-amino-3-(2-(N',N'-dimethylamino)ethyl)-1H-indole and 0.035 mMol of quinoxaline-2-carbonyl chloride, the title compound was prepared in 67% yield.

MS: m/e=374 (M$^+$)

EXAMPLE 83

N-[2-methyl-3-(2-[N',N'-dimethylamino]ethyl)-1H-indol-5-yl]-quinoline-2-carboxamide Beginning with 0.027 mMol of 2-methyl-5-amino-3-(2-(N',N'-dimethylamino)ethyl)-1H-indole and 0.035 mMol of quinoline-2-carbonyl chloride, the title compound was prepared in 86% yield.

MS: m/e=372 (M$^+$)

General Procedures for the Reductive Alkylation of Secondary Amines of Formula III Procedure A A solution of 1 equivalent amine (III), 2–3 equivalents of aldehyde, and 2 molar equivalents of sodium cyanoborohydride in 4:1 methanol:acetic acid is mixed well and allowed to stand for 24 hours at room temperature for from 3 to 24 hours. The reaction mixture is then loaded onto a VARIAN BOND ELUT SCX™ (Varian, Harbor City, Calif., U.S.A.) ion exchange column. The column is eluted with several volumes of methanol and is then eluted with either saturated methanolic hydrogen chloride or 2M ammonia in methanol. Fractions from the column containing product are concentrated under reduced pressure. Compounds eluted with methanolic hydrogen chloride provide the hydrochloride salts, and compounds eluted with ammonia in methanol provide the free bases, of compounds of the invention.

Procedure B

A solution of 1 equivalent of secondary amine (III), 1.2 equivalents of aldehyde, 12 equivalents of sodium triacetoxyborohydride, and 0.3 equivalents of acetic acid in dichloromethane is mixed for 24 hours at room temperature. The compounds of the invention are isolated as described in PROCEDURE A.

The compounds of Examples 84–89 were prepared by PROCEDURE A.

EXAMPLE 84

N-[2-methyl-3-(2-[N'-methyl-N'-(2-thienyl) methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of thiophene-2-carboxaldehyde, the title compound was prepared in 91% yield.

EXAMPLE 85

N-[2-methyl-3-(2-[N'-methyl-N'-(3-thienyl) methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of thiophene-3-carboxaldehyde, the title compound was prepared in 80% yield.

EXAMPLE 86

N-[2-methyl-3-(2-[N'-methyl-N'-(2-furyl) methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of 2-furaldehyde, the title compound was prepared in 83% yield.

EXAMPLE 87

N-[2-methyl-3-(2-[N'-methyl-N'-(2-pyridyl) methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of pyridine-2-carboxaldehyde, the title compound was prepared in 94% yield.

EXAMPLE 88

N-[2-methyl-3-(2-[N'-methyl-N'-(3-pyridyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of pyridine-3-carboxaldehyde, the title compound was prepared in 84% yield.

EXAMPLE 89

N-[2-methyl-3-(2-[N'-methyl-N'-(3-indolyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of indole-3-carboxaldehyde, the title compound was prepared in 100% yield.

The compounds of Examples 90–94 were prepared by PROCEDURE B.

EXAMPLE 90

N-[2-methyl-3-(2-[N'-methyl-N'-(1-methylpyrrol-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 1-methylpyrrole-2-carboxaldehyde, the title compound was prepared.

EXAMPLE 91

N-[2-methyl-3-(2-[N'-methyl-N'-(5-methylthien-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-methylthiophene-2-carboxaldehyde, the title compound was prepared.

EXAMPLE 92

N-[2-methyl-3-(2-[N'-methyl-N'-(5-hydroxymethylfur-2-yl methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-hydroxymethylfuran-2-carboxaldehyde, the title compound was prepared.

EXAMPLE 93

N-[2-methyl-3-(2-[N'-methyl-N'-(3-methylbenzothiophen-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 3-methylbenzothiophene-2-carboxaldehyde, the title compound was prepared.

EXAMPLE 94

N-[2-methyl-3-(2-[N'-methyl-N'-(5-chloro-1,3-benzodioxol-4-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-chloro-1,3-benzodioxole-4-carboxaldehyde, the title compound was prepared.

General Procedures for Sequential Reductive Alkylations with Aldehydes

Procedure C

An equivalent of a suitable primary amine and two equivalents of a suitable aldehyde are dissolved in methanol and shaken for 1 hour. The solution is treated with an excess of sodium borohydride and shaken for 3 hours. The reaction mixture is then passed over a VARIAN BOND ELUT SCX™ (Varian, Harbor City, Calif., U.S.A.) ion exchange column which has been preactivated with 10% acetic acid in methanol. The column is washed thoroughly with methanol and then the product is eluted with 2M ammonia in methanol. The secondary amine products are then isolated by concentration of eluant.

Procedure D

Alternatively, the reaction mixture containing the secondary amine is treated directly with an excess of a second aldehyde, acetic acid and sodium cyanoborohydride. The reaction mixture is agitated until all of the secondary amine is consumed, typically from 1 to 5 days, and the desired products isolated by subjecting the reaction mixture to the isolation procedure described in PROCEDURE C.

The compounds of Examples 95–105 were prepared by PROCEDURE C.

EXAMPLE 95

N-[2-methyl-3-(2-[N'-(fur-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of furan-2-carboxaldehyde, the title compound was prepared.

MS(m/e): 392(M+1)

EXAMPLE 96

N-[2-methyl-3-(2-[N'-(fur-3-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of furan-3-carboxaldehyde, the title compound was prepared.

MS(m/e): 391(M⁺)

EXAMPLE 97

N-[2-methyl-3-(2-[N'-(thiazol-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of thiazole-2-carboxaldehyde, the title compound was prepared.

MS(m/e): 409(M+1)

EXAMPLE 98

N-[2-methyl-3-(2-[N'-(imidazol-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of imidazole-2-carboxaldehyde, the title compound was prepared.

MS(m/e): 392(M+1)

EXAMPLE 99

N-[2-methyl-3-(2-[N'-(quinolin-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of quinoline-2-carboxaldehyde, the title compound was prepared.

MS(m/e): 452(M+)

EXAMPLE 100

N-[2-methyl-3-(2-[N'-(quinolin-4-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of quinoline-4-carboxaldehyde, the title compound was prepared.

MS(m/e): 453(M+1)

EXAMPLE 101

N-[2-methyl-3-(2-[N'-(2-phenylpropyl)amino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of 2-phenylpropanal, the title compound was prepared.

MS(m/e): 429(M+)

EXAMPLE 102

N-[2-methyl-3-(2-[N'-(5-hydroxymethylfur-2-yl)methylamino]-ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of 5-hydroxymethylfuran-2-carboxaldehyde, the title compound was prepared.

MS(m/e): 422(M+1)

EXAMPLE 103

N-[2-methyl-3-(2-[N'-(5-methylimidazol-4-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of 5-methylimidazole-2-carboxaldehyde, the title compound was prepared.

MS(m/e): 406(M+1)

EXAMPLE 104

N-[2-methyl-3-(2-[N'-(3-methylbenzothiophen-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of 3-methylbenzothiophene-2-carboxaldehyde, the title compound was prepared.

MS(m/e): 472(M+1)

EXAMPLE 105

N-[2-methyl-3-(2-[N'-(3,5-dimethyl-4-ethoxycarbonylindol-2-yl)methylamino]ethyl)-1H-indol-5-yl]-4-fluorobenzamide Beginning with 0.05 mMol of N-[2-methyl-3-(2-aminoethyl)-1H-indol-5-yl]-4-fluorobenzamide (Preparation X) and 0.1 mMol of 3,5-dimethyl-4-ethoxycarbonylindole-2-carboxaldehyde, the title compound was prepared.

MS(m/e): 491(M+1)

The compounds of Examples 106–116 were prepared by PROCEDURE D.

EXAMPLE 106

N-[2-methyl-3-(2-[N'-methyl-N'-(fur-2-yl)methylamino]ethyl)-1H-indol-5-yl]-4-fluorobenzamide Beginning with a methanol solution of N-[2-methyl-3-(2-[N'-(fur-2-yl)methylamino]ethyl)-1H-indol-5-yl]-4-fluorobenzamide (Example 95) and 0.5 mMol of paraformaldehyde, the title compound was prepared.

MS(m/e): 406(M+1)

EXAMPLE 107

N-[2-methyl-3-(2-[N'-methyl-N'-(fur-3-yl)methylamino]ethyl)-1H-indol-5-yl]-4-fluorobenzamide Beginning with a methanol solution of N-[2-methyl-3-(2-[N'-(fur-3-yl)methylamino]ethyl)-1H-indol-5-yl]-4-fluorobenzamide (Example 96) and 0.5 mMol of paraformaldehyde, the title compound was prepared.

MS(m/e) 405(M+)

EXAMPLE 108

N-[2-methyl-3-(2-[N'-methyl-N'-(thiazol-2-yl)methylamino]ethyl)-1H-indol-5-yl]-4-fluorobenzamide Beginning with a methanol solution of N-[2-methyl-3-(2-[N'-(thiazol-2-yl)methylamino]ethyl)-1H-indol-5-yl]-4-fluorobenzamide (Example 97) and 0.5 mMol of paraformaldehyde, the title compound was prepared.

MS(m/e): 423(M+1)

EXAMPLE 109

N-[2-methyl-3-(2-[N'-methyl-N'-(imidazol-2-yl)methylamino]ethyl)-1H-indol-5-yl]-4-fluorobenzamide Beginning with a methanol solution of N-[2-methyl-3-(2-[N'-(imidazol-2-yl)methylamino]ethyl)-1H-indol-5-yl]-4- fluorobenzamide (Example 98) and 0.5 mMol of paraformaldehyde, the title compound was prepared.

MS(m/e): 406(m+1)

EXAMPLE 110

N-[2-methyl-3-(2-[N'-methyl-N'-(quinolin-2-yl)methylamino]ethyl)-1H-indol-5-yl]-4-fluorobenzamide Beginning with a methanol solution of N-[2-methyl-3-(2-[N'-(quinolin-2-yl)methylamino]ethyl)-1H-indol-5-yl]-4-fluorobenzamide (Example 99) and 0.5 mMol of paraformaldehyde, the title compound was prepared.

MS(m/e): 467(M+1)

EXAMPLE 111

N-[2-methyl-3-(2-[N'-methyl-N'-(quinolin-4-yl)methylamino]ethyl)-1H-indol-5-yl]-4-fluorobenzamide Beginning with a methanol solution of N-[2-methyl-3-(2-[N'-(quinolin-4-yl)methylamino]ethyl)-1H-indol-5-yl]-4-fluorobenzamide (Example 100) and 0.5 mMol of paraformaldehyde, the title compound was prepared.

MS(m/e): 467(M+1)

EXAMPLE 112

N-[2-methyl-3-(2-[N'-methyl-N'-(2-phenylpropyl)amino]ethyl)-1H-indol-5-yl]-4-fluorobenzamide Beginning with a methanol solution of N-[2-methyl-3-(2-[N'-(2-phenylpropyl)amino]ethyl)-1H-indol-5-yl]-4-fluorobenzamide (Example 101) and 0.5 mMol of paraformaldehyde, the title compound was prepared.

MS(m/e) : 444(M$^+$)

EXAMPLE 113

N-[2-methyl-3-(2-[N'-methyl-N'-(5-hydroxymethylfur-2-yl)methylamino]ethyl)-1H-indol-5-yl]-4-fluorobenzamide Beginning with a methanol solution of N-[2-methyl-3-(2-[N'-(5-hydroxymethylfur-2-yl)methylamino]ethyl)-1H-indol-5-yl]-4-fluorobenzamide (Example 102) and 0.5 mMol of paraformaldehyde, the title compound was prepared.

MS(m/e): 436(M+1)

EXAMPLE 114

N-[2-methyl-3-(2-[N'-methyl-N'-(5-methylimidazol-4-yl)methylamino]ethyl)-1H-indol-5-yl]-4-fluorobenzamide Beginning with a methanol solution of N-[2-methyl-3-(2-[N'-(5-methylimidazol-4-yl)methylamino]ethyl)-1H-indol-5-yl]-4-fluorobenzamide (Example 103) and 0.5 mMol of paraformaldehyde, the title compound was prepared.

MS(m/e): 420(M+1)

EXAMPLE 115

N-[2-methyl-3-(2-[N'-methyl-N'-(3-methylbenzothiophen-2-yl)methylamino]ethyl)-1H-indol-5-yl]-4-fluorobenzamide Beginning with a methanol solution of N-[2-methyl-3-(2-[N'-(3-methylbenzothiophen-2-yl)methylamino]ethyl)-1H-indol-5-yl]-4-fluorobenzamide (Example 104) and 0.5 mMol of paraformaldehyde, the title compound was prepared.

MS(m/e): 486(M$^+$)

EXAMPLE 116

N-[2-methyl-3-(2-[N'-methyl-N'-(3,5-dimethyl-4-ethoxycarbonylindol-2-yl)methylamino]ethyl)-1H-indol-5-yl]-4-fluorobenzamide Beginning with a methanol solution of N-[2-methyl-3-(2-[N'-(3,5-dimethyl-4-ethoxycarbonylindol-2-yl)methylamino]ethyl)-1H-indol-5-yl]-4-fluorobenzamide (Example 105) and 0.5 mMol of paraformaldehyde, the title compound was prepared.

MS(m/e): 506(M+1)

General Procedure for Reductive Alkylations with Ketones

Procedure E

An equivalent of a suitable primary amine and two equivalents of a suitable ketone are dissolved in methanol containing acetic acid. The solution is treated with an excess of sodium cyanoborohydride and agitated until sufficient product has been formed, typically for from 1–5 days. The reaction mixture is then passed over a VARIAN BOND ELUT SCX™ (Varian, Harbor City, Calif., U.S.A.) ion exchange column which has been preactivated with 10% acetic acid in methanol. The column is washed thoroughly with methanol and then the product is eluted with 2M ammonia in methanol. The secondary amine products are then isolated by concentration of eluant.

The compounds of Examples 117 and 118 were prepared by PROCEDURE E.

EXAMPLE 117

N-[2-methyl-3-(2-[N'-isopropylamino]ethyl)-1H-indol-5-yl]-4-fluorobenzamide

Beginning with 0.05 mMol of N-[2-methyl-3-(2-aminoethyl)-1H-indol-5-yl]-4-fluorobenzamide (Preparation X) and 0.1 mMol of acetone, the title compound was prepared.

MS(m/e): 354(M+1)

EXAMPLE 118

N-[2-methyl-3-(2-[N'-cyclohexylamino]ethyl)-1H-indol-5-yl]-4-fluorobenzamide

Beginning with 0.05 mMol of N-[2-methyl-3-(2-aminoethyl)-1H-indol-5-yl]-4-fluorobenzamide (Preparation X) and 0.1 mMol of cyclohexanone, the title compound was prepared.

MS(m/e): 394(M+1)

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90, 408–412 (1993).

Membrane Preparation: Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (*Biochem. Pharmacol.*, 22, 3099–3108 (1973). All experiments were performed in triplicate. Representative compounds of the present invention were found to have an affinity at the 5-HT$_{1F}$ receptor of K$_i$≦1.5 mM.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1 -piperazineethanesulfonic acid) and 10 μM pargyline for 20 minutes at 37° C., 5% CO$_2$. Drug dose-effect curves were then conducted by adding 6 different final concentrations of drug, followed immediately by the addition of forskolin (10 μM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 μM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software.

The discovery that the pain associated with migraine and associated disorders is inhibited by agonists of the 5-HT$_{1F}$ receptor required the analysis of data from diverse assays of pharmacological activity. To establish that the 5-HT$_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-HT$_{1F}$ receptor subtype was performed as described supra. For comparison purposes, the binding affinities of compounds to the 5-HT$_{1D\alpha}$, 5-HT$_{1D\beta}$, 5-HT$_{1E}$ and 5-HT$_{1F}$ receptors were also determined as described supra, except that different cloned receptors were employed in place of the 5-HT$_{1F}$ receptor clone employed therein. The same panel was then tested in the cAMP assay to determine their agonist or antagonist character at each of the 5-HT$_{1D\alpha}$, 5-HT$_{1D\beta}$, 5-HT$_{1E}$ and 5-HT$_{1F}$ receptor subtypes. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I

3-[2-(dimethylamino)ethyl]-N-methyl-1H-indole-5-methanesulfonamide butane-1,4-dioate (1:1)
(Sumatriptan succinate)

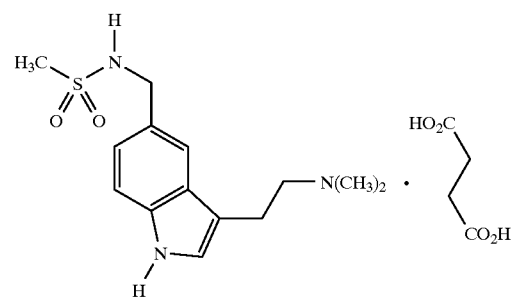

Sumatriptan succinate is commercially available as Imitrex™ or may be prepared as described in U.S. Pat. No. 5,037,845, issued Aug. 6, 1991, which is herein incorporated by reference.

51

Compound II 5-fluoro-3-<1-<2-<1-methyl-1H-pyrazol-4-yl>ethyl>-4-piperidinyl>-1H-indole hydrochloride

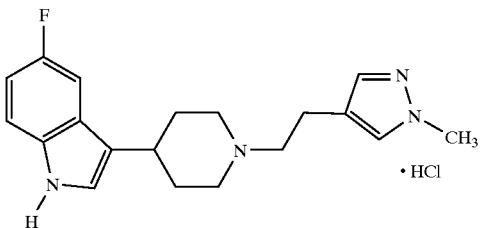

Compound II is described in U.S. Pat. No. 5,521,196, issued May 28, 1996, which is herein incorporated by reference in its entirety.

Compound III 5-hydroxy-3-(4-piperidinyl)-1H-indole oxalate

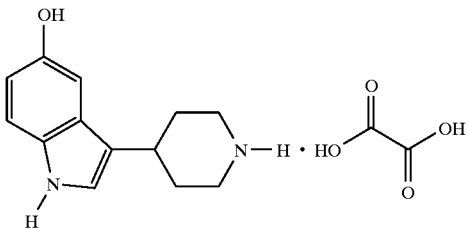

Compound III is available by the following procedure.

5-benzyloxy-3-[1,2,5,6-tetrahydro-4-pyridinyl]-1H-indole

Starting with 5.0 gm (22 mMol) 5-benzyloxyindole and 6.88 gm (45 mMol) 4-piperidone.HCl.H$_2$O, 6.53 gm (97.6%) of 5-benzyloxy-3-[1,2,5,6-tetrahydro-4-pyridinyl]-1H-indole were recovered as a light yellow solid by the procedure described in Preparation I. The material was used in the subsequent step without further purification.

Hydrogenation/Hydrogenolysis

To a solution of 1.23 gm (4 mMol) 5-benzyloxy-3-[1,2,5,6-tetrahydro-4-pyridinyl]-1H-indole in 50 mL 1:1 tetrahydrofuran:ethanol were added 0.3 gm 5% palladium on carbon and the reaction mixture hydrogenated at ambient temperature for 18 hours with an initial hydrogen pressure of 60 p.s.i. The reaction mixture was then filtered through a celite pad and the filtrate concentrated under reduced pressure. The residue was converted to the oxalate salt and 0.98 gm (80.0%) of Compound III were recovered as a brown foam.

m.p.=67° C.

MS(m/e): 216(M$^+$)

Calculated for $C_{13}H_{16}N_2O \cdot C_2H_2O_4$: Theory: C, 58.81; H, 5.92; N, 9.14. Found: C, 58.70; H, 5.95; N, 9.39.

52

Compound IV 8-chloro-2-diethylamino-1,2,3,4-tetrahydronaphthalene hydrochloride

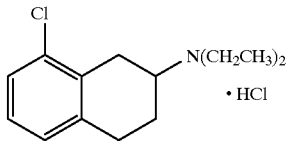

Compound IV is available by the following procedure.

8-chloro-2-tetralone

A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0%) of o-chlorophenylacetyl chloride as a transparent, pale yellow, mobile liquid.

NMR(CDCl$_3$): 7.5–7.1 (m, 4H), 4.2 (s, 2H).

To a slurry of 46.5 gm (0.348 mole) AlCl$_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane:diethyl ether to give 10.55 gm of the title compound.

NMR(CDCl$_3$): 7.5–7.2 (m, 3H), 3.7 (s, 2H), 3.3–3.0 (t, J=7 Hz, 2H), 2.8–2.4 (t, J=7 Hz, 2H).

MS: 180(60), 165(9), 138(100), 117(52), 115(50), 103 (48), 89(20), 76(25), 74(18), 63(30), 57(9), 52(28), 51(20), 42(6), 39(32).

IR(nujol mull): 2950 cm$^{-1}$, 2927 cm$^{-1}$, 1708 cm$^{-1}$, 1464 cm$^{-1}$, 1450 cm$^{-1}$, 1169 cm$^{-1}$, 1141 cm$^{-1}$.

Reductive Amination

To a solution of 0.5 gm (2.78 mMol) 8-chloro-2-tetralone in 25 mL cyclohexane were added 1.4 mL (13.9 mMol) diethylamine followed by 0.1 gm p-toluenesulfonic acid monohydrate. The reaction mixture was then heated at reflux with constant water removal (Dean-Stark Trap) for 18 hours. The reaction mixture was then cooled to ambient and the volatiles removed under reduced pressure. The residue was then dissolved in 15 mL methanol to which were then added 1.5 mL acetic acid followed by the portionwise addition of 0.5 gm sodium borohydride. The reaction mixture was then stirred for 1 hour at ambient.

The reaction mixture was then diluted with 20 mL 10% HCl and stirred for an additional hour. The mixture was then extracted with diethyl ether and the remaining aqueous phase was poured over ice, made basic with ammonium hydroxide and extracted well with dichloromethane. These extracts were combined, dried over sodium sulfate and concentrated under reduced pressure. The residue was redissolved in dichloromethane and subjected to chromatography over basic alumina, eluting with dichloromethane. Fractions shown to contain product were combined and concentrated under reduced pressure. The residual oil was dissolved in diethyl ether and the solution saturated with hydrogen chloride. The viscous residue was crystallized from acetone/diethyl ether to give 0.20 gm (23.2%) of Compound IV as colorless crystals.

m.p.=158–159° C.
MS(m/e): 273
Calculated for $C_{14}H_{21}NCl·HCl$: Theory: C, 61.32; H, 7.72; N, 5.11. Found: C, 61.62; H, 7.94; N, 5.03.

Compound V 6-hydroxy-3-dimethylamino-1,2,3,4-tetrahydrocarbazole

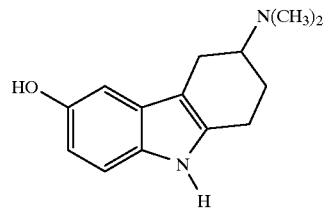

Compound V is available by the following procedure.
4-dimethylamino-1-cyclohexanone ethylene ketal To a solution of 5.0 gm (32 mMol) 1,4-cyclohexanedione mono-ethylene ketal and 10.80 gm (240 mMol) dimethylamine were added 2.0 mL acetic acid and the mixture was stirred at 0° C. for 1.5 hours. To this solution were then added 3.62 gm (58 mMol) sodium cyanoborohydride and the reaction stirred for an additional hour at ambient. The pH of the reaction mixture was adjusted to ~7 with 16 mL acetic acid and stirred 18 hours at ambient. The volatiles were removed under reduced pressure and the residue dissolved in cold 5% tartaric acid solution and then the aqueous phase was made basic with 5N sodium hydroxide. This aqueous phase was extracted well with dichloromethane. These organic extracts were combined and concentrated under reduced pressure to give 5.04 gm (85%) of the title compound as an oil.

4-dimethylamino-1-cyclohexanone 4.96 gm (26.8 mMol) 4-dimethylamino-1-cyclohexanone ethylene ketal were dissolved in 50 mL formic acid and the solution stirred at reflux for 18 hours. The reaction mixture was then cooled to ambient and the volatiles removed under reduced pressure to give 3.78 gm (100%) of the title compound.

6-benzyloxy-3-dimethylamino-1,2,3,4-tetrahydrocarbazole

To a solution of 3.78 gm (26.8 mMol) 4-dimethylamino-1-cyclohexanone and 6.69 gm (26.8 mMol) 4-benzyloxyphenylhydrazine hydrochloride in 50 mL ethanol were added 2.17 mL (26.8 mMol) pyridine. To this solution were added 5×10 mL portions of water and the reaction mixture then stored at 0° C. for 18 hours. The reaction mixture was then diluted with an additional 50 mL of water and the mixture extracted well with dichloromethane. The combined organic extracts were dried over sodium sulfate and the volatiles removed under reduced pressure. The residual oil was subjected to flash silica gel chromatography, eluting with 9:1 chloroform:methanol. Fractions shown to contain the desired product were combined and concentrated under reduced pressure to give 2.14 gm (24.9%) of the title compound.

Hydrogenolysis

To a solution of 2.14 gm (6.7 mMol) 6-benzyloxy-3-dimethylamino-1,2,3,4-tetrahydrocarbazole in 50 mL ethanol were added 0.20 gm 10% palladium on carbon and the reaction mixture was hydrogenated at ambient temperature with an initial hydrogen pressure of 40 p.s.i. After 5 hours an additional charge of 0.20 gm 10% palladium on carbon were added and the reaction mixture repressurized with hydrogen to 40 p.s.i. for 4 hours. The reaction mixture was then filtered through a pad of celite and the filtrate concentrated under reduced pressure. The residue was subjected to Florisil chromatography, eluting with 9:1 chloroform:methanol. Fractions shown to contain the desired compound were combined and concentrated under reduced pressure. The residue was again subjected to Florisil chromatography, eluting with a gradient consisting of chloroform containing 2–10% methanol. Fractions shown to contain product were combined and concentrated under reduced pressure to give Compound V as a crystalline solid.

MS(m/e): 230($M^+$)
Calculated for $C_{14}H_{18}N_2O$: Theory: C, 73.01; H, 7.88; N, 12.16. Found: C, 72.75; H, 7.83; N, 11.97.

Binding Assays

The binding affinities of compounds for various serotonin receptors were determined essentially as described above except that different cloned receptors are employed in place of the 5-$HT_{1F}$ receptor clone employed therein. The results of these binding experiments are summarized in Table II.

TABLE II

| BINDING TO SEROTONIN (5-$HT_1$) RECEPTOR SUBTYPES ($K_i$ nM) | | | | |
|---|---|---|---|---|
| Compound | 5-$HT_{1D\alpha}$ | 5-$HT_{1D\beta}$ | 5-$HT_{1E}$ | 5-$HT_{1F}$ |
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-$HT_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at –3.5 mm for rats or –4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 μm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. This data is presented in Table III.

TABLE III

Inhibition of Protein Extravasation ($ID_{50}$ mMol/kg)

| Compound | i.v. $ID_{50}$ (mMol/kg) |
|---|---|
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the $5\text{-}HT_{1D\alpha}$, $5\text{-}HT_{1D\beta}$, $5\text{-}HT_{1E}$ and $5\text{-}HT_{1F}$ receptors was plotted against their $ID_{50}$ in the protein extravasation model. A linear regression analysis was performed on each set of data and a correlation factor, $R^2$, calculated. The results of this analysis are summarized in Table IV.

TABLE IV

Correlation Factor ($R^2$) for Specific $5\text{-}HT_1$ Subtype Binding Affinity vs Inhibition of Protein Extravasation

| $5\text{-}HT_1$ Subtype | Correlation Factor ($R^2$) |
|---|---|
| $5\text{-}HT_{1D\alpha}$ | 0.07 |
| $5\text{-}HT_{1D\beta}$ | 0.001 |

TABLE IV-continued

Correlation Factor ($R^2$) for Specific $5\text{-}HT_1$ Subtype Binding Affinity vs Inhibition of Protein Extravasation

| $5\text{-}HT_1$ Subtype | Correlation Factor ($R^2$) |
|---|---|
| $5\text{-}HT_{1E}$ | 0.31 |
| $5\text{-}HT_{1F}$ | 0.94 |

An ideally linear relationship would generate a correlation factor of 1.0, indicating a cause and effect relationship between the two variables. The experimentally determined correlation factor between inhibition of neuronal protein extravasation and $5\text{-}HT_{1F}$ binding affinity is 0.94. This nearly ideal dependence of the $ID_{50}$ in the protein extravasation model on binding affinity to the $5\text{-}HT_{1F}$ receptor clearly demonstrates that the $5\text{-}HT_{1F}$ receptor mediates the inhibition of protein extravasation resulting from stimulation of the trigeminal ganglia.

The compounds of the present invention are distinguished from structurally similar tryptamines by their lack of vasoconstrictive properties. The lack of vasoconstrictive activity exhibited by the compounds of the present invention was determined by measuring their ability to mediate vasoconstriction in the rabbit saphenous vein.

Rabbit Saphenous Vein Contraction

Male New Zealand White rabbits (3–6 lbs) (Hazleton, Kalamazoo, Mich.) were sacrificed by a lethal dose of sodium pentobarbital (325 mg) injected into the ear vein. Tissues were dissected free of connective tissue, cannulated in situ with polyethylene tubing (PE50, outside diameter= 0.97 mm) and placed in petri dishes containing Kreb's bicarbonate buffer (described infra). The tips of two 30-gauge stainless steel hypodermic needles bent into an L-shape were slipped into the polyetylene tubing. Vessels were gently pushed from the cannula onto the needles. The needles were then separated so that the lower one was attached with thread to a stationary glass rod and the upper one was tied with thread to the transducer.

Tissues were mounted in organ baths containing 10 mL of modified Krebs' solution of the following composition: 118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$. Tissue bath solutions were maintained at 37° C. and aerated with 95% $O_2$ and 5% $CO_2$. An initial optimum resting force of 1 gm was applied to the saphenous vein. Isometric contractions were recorded as changes in grams of force on a Beckman Dynograph with Statham UC-3 transducers and microscale accessory attachments. Tissues were allowed to equilibrate 1 to 2 hours before exposure to drugs. Cumulative agonist concentration-response curves were generated in tissues and no tissue was used to generate more than two agonist concentration-response curves. All results were expressed as a mean $EC_{50}$ and the maximal response was expressed as a percentage of the response to 67 mM KCl administered initially in each tissue.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 1 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 106 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:
1. A compound of Formula II:

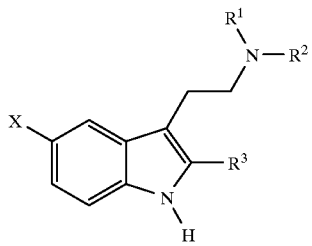

in which
$R^1$ is hydrogen or $C_1-C_4$ alkyl;
$R^2$ is $C_1-C_4$ alkyl, $C_3-C_8$ cycloalkyl, cycloalkyl-$(C_1-C_3$ alkylene), aryl-$(C_1-C_3$ alkylene), or heteroaryl-$(C_1-C_3$ alkylene);
$R^3$ is hydrogen or $C_1-C_4$ alkyl;
X is $R^4C(O)NH-$, $R^5R^6NC(Y)NH-$, $R^7OC(O)NH-$, or $R^8SO_2NH-$;
$R^4$ is $C_1-C_4$ alkyl, $C_3-C_7$ cycloalkyl, phenyl, substituted phenyl, biphenylyl, naphthyl, or a heterocycle;
$R^5$ and $R^6$ are independently selected from the group consisting of hydrogen, $C_1-C_6$ alkyl, $C_3-C_6$ alkenyl, $C_3-C_8$ cycloalkyl, phenyl, substituted phenyl, phenyl $(C_1-C_4$ alkylene), phenyl$(C_1-C_4$ alkylene) substituted in the phenyl ring, $((C_1-C_4$ alkyl or $C_1-C_4$ alkoxycarbonyl substituted)$C_1-C_4$ alkyl)phenyl, $C_1-C_4$ alkyl α-substituted with $C_1-C_4$ alkoxycarbonyl; or
$R^5$ and $R^6$ taken together with the nitrogen atom to which they are attached form a pyrrolidine, piperidine, piperazine, 4-substituted piperazine, morpholine or thiomorpholine ring;
$R^7$ is $C_1-C_6$ alkyl, $C_3-C_6$ alkenyl, phenyl, substituted phenyl, $C_3-C_8$ cycloalkyl, $C_1-C_4$ alkyl ω-substituted with $C_1-C_4$ alkoxy;
$R^8$ is $C_1-C_4$ alkyl, phenyl, substituted phenyl, or di$(C_1-C_4$ alkyl)amino;
Y is S or O, and pharmaceutically acceptable acid addition salts thereof subject to the following provisos:
1) $R^1$ and $R^3$ may be hydrogen only when $R^2$ is heteroaryl$(C_1-C_4$ alkylene); and
2) X may be $R^5R^6NC(Y)NH-$, $R^7OC(O)NH-$, or $R^8SO_2NH-$ only when $R^2$ is heteroaryl$(C_1-C_4$ alkylene).
2. A compound of claim 1 where X is $R^4C(O)NH-$.
3. A compound of claim 2 where $R^4$ is a heterocycle.
4. A compound of claim 2 where $R^4$ is phenyl or substituted phenyl.
5. A compound of claim 4 where $R^1$ is $C_1-C_4$ alkyl.
6. A compound of claim 2 where $R^3$ is methyl.
7. A compound of claim 5 where $R^1$ is methyl.
8. A compound of claim 1 where $R^2$ is heteroaryl-$(C_1-C_3$ alkylene).
9. A compound of claim 1 which is N-[2-methyl-3-(2-[N'-methyl-N'-(fur-2-yl)methylamino]ethyl)-1H-indol-5-yl]-4-fluorobenzamide and pharmaceutically acceptable salts thereof.

10. A method for the treatment of migraine comprising administering to a mammal suffering from migraine an effective amount of a compound of claim 1.
11. The method of claim 10 where the mammal is a human.
12. A pharmaceutical formulation which comprises, in association with a pharmaceutically acceptable carrier, diluent or excipient, a compound of claim 1.
13. A method for activation of 5-$HT_{1F}$ receptors in mammals comprising administering to a mammal in need of such activation a pharmaceutically effective amount of a compound of Formula I:

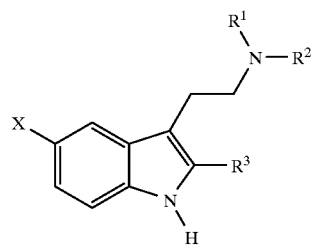

in which
$R^1$ is hydrogen or $C_1-C_4$ alkyl;
$R^2$ is $C_1-C_4$ alkyl, $C_3-C_8$ cycloalkyl, cycloalkyl-$(C_1-C_3$ alkylene), aryl-$(C_1-C_3$ alkylene), or heteroaryl-$(C_1-C_3$ alkylene);
$R^3$ is hydrogen or $C_1-C_4$ alkyl;
X is $R^4C(O)NH-$, $R^5R^6NC(Y)NH-$, $R^7OC(O)NH-$, or $R^8SO_2NH-$;
$R^4$ is $C_1-C_4$ alkyl, $C_3-C_7$ cycloalkyl, phenyl, substituted phenyl, biphenylyl, naphthyl, or a heterocycle;
$R^5$ and $R^6$ are independently selected from the group consisting of hydrogen, $C_1-C_6$ alkyl, $C_3-C_6$ alkenyl, $C_3-C_8$ cycloalkyl, phenyl, substituted phenyl, phenyl $(C_1-C_4$ alkylene), phenyl$(C_1-C_4$ alkylene) substituted in the phenyl ring, $((C_1-C_4$ alkyl or $C_1-C_4$ alkoxycarbonyl substituted)$C_1-C_4$ alkyl)phenyl, $C_1-C_4$ alkyl α-substituted with $C_1-C_4$ alkoxycarbonyl; or
$R^5$ and $R^6$ taken together with the nitrogen atom to which they are attached form a pyrrolidine, piperidine, piperazine, 4-substituted piperazine, morpholine or thiomorpholine ring;
$R^7$ is $C_1-C_6$ alkyl, $C_3-C_6$ alkenyl, phenyl, substituted phenyl, $C_3-C_8$ cycloalkyl, $C_1-C_4$ alkyl ω-substituted with $C_1-C_4$ alkoxy;
$R^8$ is $C_1-C_4$ alkyl, phenyl, substituted phenyl, or di$(C_1-C_4$ alkyl)amino;
Y is S or O, and pharmaceutically acceptable acid addition salts thereof.

* * * * *